(12) United States Patent
Hwang et al.

(10) Patent No.: US 10,485,868 B2
(45) Date of Patent: *Nov. 26, 2019

(54) TN VACCINE COMPOSITION AND METHOD FOR ALLEVIATING INFLAMMATION

(71) Applicant: TAIPEI MEDICAL UNIVERSITY, Taipei (TW)

(72) Inventors: Jaulang Hwang, Taipei (TW); Chung-Ming Chen, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/709,273

(22) Filed: Sep. 19, 2017

(65) Prior Publication Data
US 2019/0083613 A1    Mar. 21, 2019

(51) Int. Cl.
| | | |
|---|---|---|
| A61K 39/395 | (2006.01) | |
| A61P 11/00 | (2006.01) | |
| A61K 47/64 | (2017.01) | |
| C07K 16/24 | (2006.01) | |

(52) U.S. Cl.
CPC ...... *A61K 39/39558* (2013.01); *A61K 47/646* (2017.08); *A61P 11/00* (2018.01); *C07K 16/241* (2013.01)

(58) Field of Classification Search
CPC .............. A61K 39/39558; A61K 47/68; A61K 47/646; A61K 2300/00; A61K 47/6853; A61K 47/6857; A61K 47/6863; A61K 47/6867; A61K 47/6859; A61K 47/64; A61K 47/6861; A61K 47/6811; A61K 47/6813; A61K 51/1045; A61K 39/0011; A61P 11/00; C07K 16/241; C07K 16/30; C07K 2319/00

See application file for complete search history.

(56) References Cited

U.S. PATENT DOCUMENTS

| | | |
|---|---|---|
| 8,383,767 B2 | 2/2013 | Hwang et al. |
| 2003/0170249 A1 | 9/2003 | Hakomori et al. |
| 2007/0275019 A9 | 11/2007 | Hakomori et al. |
| 2009/0324619 A1* | 12/2009 | Hwang ............... A61K 39/00 424/178.1 |
| 2010/0278818 A1 | 11/2010 | Hubert-Haddad et al. |

OTHER PUBLICATIONS

Ho CW, Lin CY, Liaw YW, Chiang HL, Chin YT, Huang RL, Lai HC, Hsu YW, Kuo PJ, Chen CE, Lin HY, Whang-Peng J, Nieh S, Fu E, Liu LF, Hwang J. The cytokine-cosmc signaling axis upregulates the tumor-associated carbohydrate antigen Tn. Oncotarget. Sep. 20, 2016;7(38):61930-61944.*

Brooks CL, Schietinger A, Borisova SN, Kufer P, Okon M, Hirama T, Mackenzie CR, Wang LX, Schreiber H, Evans SV. Antibody recognition of a unique tumor-specific glycopeptide antigen. Proc Natl Acad Sci U S A. Jun. 1, 2010;107(22):10056-61. doi: 10.1073/pnas.0915176107. Epub May 17, 2010.*

Li Q, Anver MR, Butcher DO, Gildersleeve JC. Resolving conflicting data on expression of the Tn antigen and implications for clinical trials with cancer vaccines. Mol Cancer Ther. Apr. 2009;8(4):971-9.*

Ganneau C, Simenel C, Emptas E, Courtiol T, Coïc YM, Artaud C, Dériaud E, Bonhomme F, Delepierre M, Leclerc C, Lo-Man R, Bay S. Large-scale synthesis and structural analysis of a synthetic glycopeptide dendrimer as an anti-cancer vaccine candidate. Org Biomol Chem. Dec. 20, 2016;15(1):114-123.*

Holmberg LA, Sandmaier BM. Vaccination with Theratope (STn-KLH) as treatment for breast cancer. Expert Rev Vaccines. Dec. 2004;3(6):655-63.*

Ta A, Harpaz N, Bodian C, Roston A, Oberman L, Chen A, Itzkowitz S. Sialyl-tn antigen expression in Crohn's colitis. Inflamm Bowel Dis. 1997 Winter;3(4):254-9.*

Ishino H, Kawahito Y, Hamaguchi M, Takeuchi N, Tokunaga D, Hojo T, Wada M, Yamamoto A, Kadoya M, Tsubouchi Y, Kohno M, Nakada H. Expression of Tn and sialyl Tn antigens in synovial tissues in rheumatoid arthritis. Clin Exp Rheumatol. Mar.-Apr. 2010;28(2):246-9. Epub May 13, 2010.*

Petrovsky N. Comparative Safety of Vaccine Adjuvants: A Summary of Current Evidence and Future Needs. Drug Saf. Nov. 2015;38 (11):1059-74.*

Awate S, Babiuk LA, Mutwiri G. Mechanisms of action of adjuvants. Front Immunol. May 16, 2013;4:114.*

Lal CV, Ambalavanan N. Genetic predisposition to bronchopulmonary dysplasia. Semin Perinatol. Dec. 2015;39(8):584-91. Epub Oct. 23, 2015.*

Chiang, Hsiao-Ling, et al., A Novel Synthetic Bipartite Carrier Protein for Developing Glycotope-Based Vaccines, *Vaccine*, Dec. 14, 2012; 30(52): 7573-7581.

Herati, Ramin Sedaghat, et al., What is the Predictive Value of Animal Models for Vaccine Efficacy in Humans? Consideration of Strategies to Improve the Value of Animal Models, *Cold Springs Harbor Perspectives in Biology*, Mar. 27, 2017, Published in Advance Mar. 27, 2017, doi 10.1101/cshperspect.a031583.

Ho, Chia-Wen, et al., The cytokine-cosmc signaling axis upregulates the tumor-associated carbohydrate antigen TN, *Oncotarget*, Sep. 20, 2016; 7(38): 61930-61944.

Wright, Clyde J., et al., Manipulation of Gene Expression by Oxygen: A Primer Form Bedside to Bench, *Pediatr Res.*, Jul. 2009; 66(1): 3-10.

* cited by examiner

*Primary Examiner* — Rachel B Gill
(74) *Attorney, Agent, or Firm* — Duane Morris LLP

(57) ABSTRACT

The present invention develops a vaccine composition against and treatment or prevention on inflammation and lung injury (particularly hyperoxia-induced lung injury) and progression of periodontitis. Tn immunization increases serum anti-Tn antibody titers, while it decreases lavaged protein and cytokines, and also decreases mean linear intercept and lung injury score. Furthermore, the improvement in lung injury is accompanied by a decrease in NF-κB activity.

12 Claims, 20 Drawing Sheets
(11 of 20 Drawing Sheet(s) Filed in Color)
Specification includes a Sequence Listing.

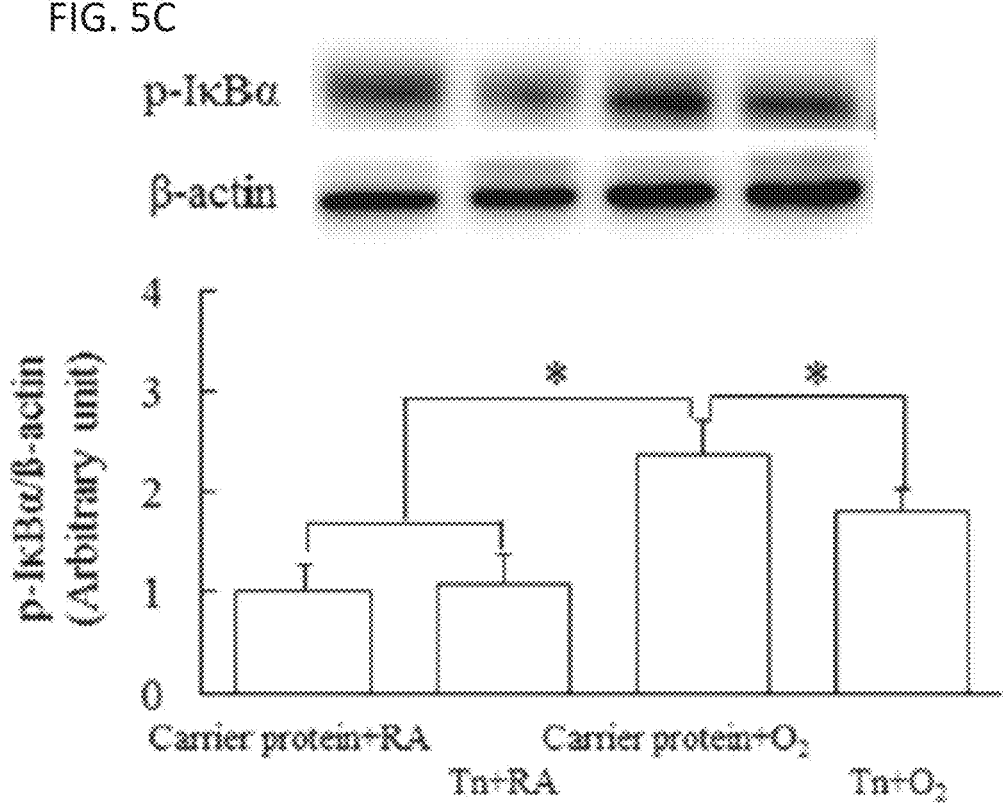

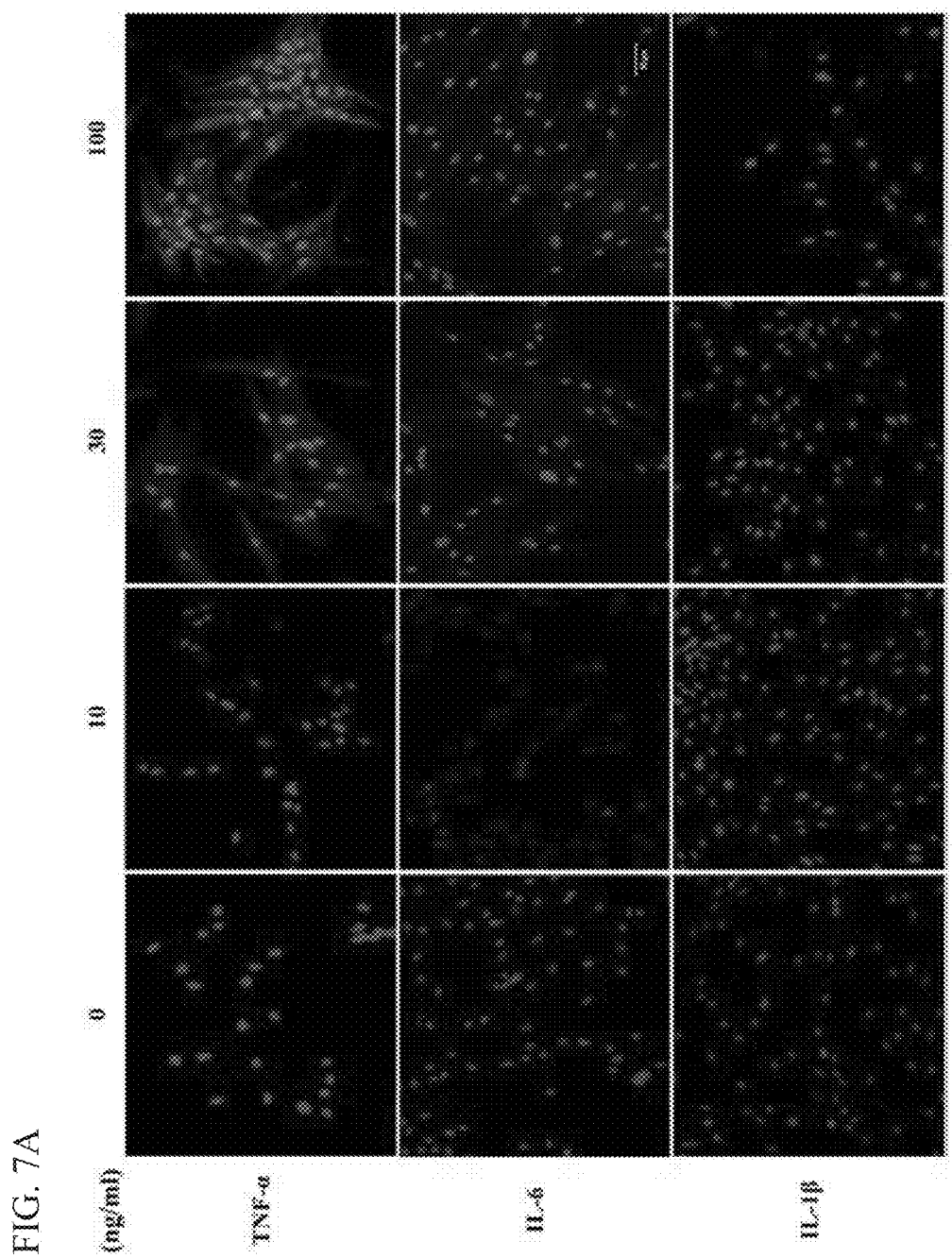

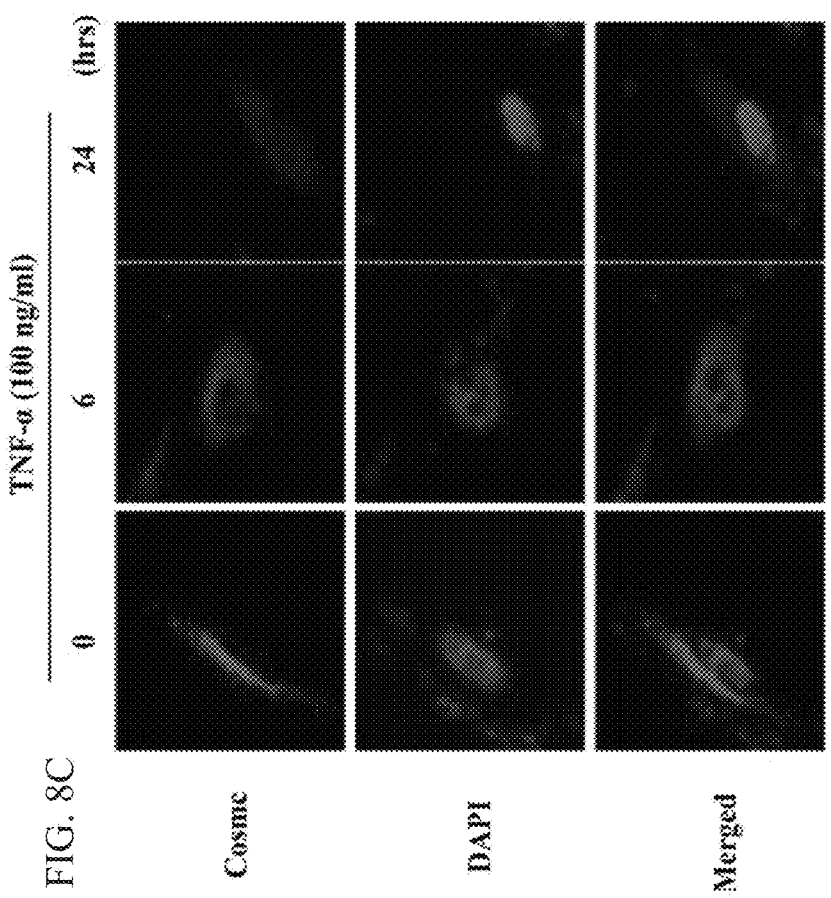

TN VACCINE COMPOSITION AND METHOD FOR ALLEVIATING INFLAMMATION

FIELD OF THE INVENTION

The invention relates to the field of treatment of inflammation-related diseases. Particularly, the invention relates to use of TN immunogen in reducing cytokines and treating inflammation-related diseases.

SEQUENCE LISTING

The instant application contains a Sequence Listing which has been submitted electronically in ASCII format and is hereby incorporated by reference in its entirety. Said ASCII copy, created on Dec. 12, 2017, is named G4590-01300_SL.txt and is 1 KB in size.

BACKGROUND OF THE INVENTION

Tn antigen (GalNAc-a-O-Ser/Thr), a mucin-type O-linked glycan, is a well-established cell surface marker for tumors. Elevated levels are correlated with cancer progression and prognosis. Tn antigen is found abnormally overexpressed in various cancers by inhibiting the further extension of glycosylation. The substrate specificity and specific molecular chaperon of T-synthase core 1 β3-Gal-T-specific molecular chaperone (Cosmc) have also been demonstrated by previous studies. Thus, either a defective T-synthase or decreased expression of Cosmc could prevent the extension of O-linked glycosylation of mucin, resulting in an apparently increased expression of Tn antigen. When further extension of O-linked glycosylation is blocked, Tn antigen can also be further modified with sialic acid residue by alpha-2,6-sialyltransferase to generate sialyl Tn (NeuAca6GalNAc-Ser/Thr, sTn). US 20030170249 and US20070275019 provide a vaccine comprising: (a) a pharmaceutically effective amount of a carbohydrate antigen found on said cancer cells, or a mimetic thereof; and (b) a pharmaceutically acceptable carrier. The carbohydrate antigen can be Tn or sialyl-Tn. US 20100278818 provides a pharmaceutical composition comprising an antibody, directed against Tn antigen. U.S. Pat. No. 8,383,767 found that coupling a glycoantigen Tn, sTn, or GM3 with a protein carrier containing an immunoglobulin (Ig) Fc domain and a cysteine-rich domain significantly improved its antigenicity. Chiang et al. developed an anti-Tn vaccine, which induces anti-Tn antibodies in mice with high specificity and high affinity using linear array epitope technology (H. L. Chiang, C. Y. Lin, F. D. Jan, Y. S. Lin, C. T. Hsu, J. Whang-Peng, L. F. Liu, S. Nieh, C. C. Lin, J. Hwang, *A novel synthetic bipartite carrier protein for developing glycotope-based vaccines. Vaccine* 30 (2012)7573-7581).

There are also reports that Tn is elevated in inflammatory tissues; the expression of Tn is associated with the extent of inflammatory response upon tissue damage. For example, Tn syndrome is characterized by the detection of Tn antigen on blood cells of all lineages. Tn antigen can be detected on the IgA1 hinge region in some IgA nephropathy patients. Additionally, Tn is known to express in chronic inflammatory tissues such as those from patients with rheumatoid arthritis and osteoarthritis. Elevated Tn expression has been observed in inflammation-inflicted tissue damage and found to be associated with modulation of the host immune response.

Hyperoxia increases NF-κB translocation in fetal and adult lung fibroblasts and the production of proinflammatory mediators such as tumor necrosis factor-α (TNF-α), interferon-γ, and interleukin-1β (IL-1β) (H. D. Li, Q. X. Zhang, Z. Mao, X. J. Xu, N. Y. Li, H. Zhang, *Exogenous interleukin-10 attenuates hyperoxia-induced acute lung injury in mice. Exp. Physiol.* 100 (2015) 331-330; and C. J. Wright, P. A. Dennery, *Manipulation of gene expression by oxygen: a primer from bedside to bench. Pediatr. Res.* 66 (2009) 3-10). Prolonged exposure to hyperoxia leads to inflammation and acute lung injury. No effective therapies have yet been established.

SUMMARY OF THE INVENTION

The present invention provides a vaccine, comprising about 0.1 mg to about 4 mg of a Tn immunogen per dose and a pharmaceutically acceptable adjuvant solution in a ratio of about 0.5 to about 2 (v/v) to about 0.5 to about 2 (v/v). In one embodiment, the ratio of Tn immunogen to the adjuvant solution is about 1 (v/v):about 1 (v/v). In one embodiment, the vaccine comprises about 0.1 mg to about 2 mg of a Tn immunogen per dose in a therapeutically effective and pharmaceutically acceptable adjuvant formulation.

The present invention provides a method of inducing an immune response in a subject to treat and/or prevent an inflammatory disease (e.g. inflammation), comprising administering a single dose vaccine comprising about 0.1 mg to about 2 mg of a Tn immunogen to the subject. In one embodiment, the single dose vaccine comprises about 0.1 mg to about 2 mg of a Tn immunogen per dose and an adjuvant solution in a ratio of about 0.5 to about 2 (v/v) to about 0.5 to about 2 (v/v).

The invention also provides a method of inducing an immune response in a subject to treat or prevent an inflammation disease, comprising administering about 0.1 mg to about 2 mg of a Tn immunogen per dose to the subject at least four times at biweekly intervals. In one embodiment, the method further comprises an additional immunization one week after the fourth immunization. In one embodiment, the additional immunization can be conducted one or more times after the last immunization. In one embodiment, the single dose vaccine comprises about 0.1 mg to about 2 mg of a Tn immunogen per dose and an adjuvant solution in a ratio of about 0.5 to about 2 (v/v) to about 0.5 to about 2 (v/v).

The inflammation disease is progression of periodontitis, organ injury or organ fibrosis. In one embodiment, the organ injury is lung injury, renal injury or liver injury. In another embodiment, the lung injury is hyperoxia-induced lung injury.

The method of the present invention can reduce the levels of interleukine-6 (IL-6) and TNF-α and reduce the activity of NF-κB in a cell or a subject. According to the invention, the cell or the subject has an elevated Tn expression and the Tn expression is upregulated by TNF-α and IL-6. Furthermore, the elevated Tn levels is commonly regulated by the cytokine-Cosmc signaling axis.

The Tn immunogen can be conjugated with a carrier polypeptide at a weight ratio of about 3 to about 8:about 1. The carrier protein is an antigen presenting cell (APC) binding domain and or a cysteine-rich domain. In some embodiments, the cysteine-rich domain contains 6 cysteine residues (SEQ ID NO: 1); preferably, the cysteine-rich domain has the amino acid sequence of Pro-Cys-Cys-Gly-Cys-Cys-Gly-Cys-Gly-Cys (SEQ ID NO: 2). In another further embodiment, the cysteine-rich domain contains 2 to 30 repeats of the amino acid sequence.

The Tn immunogen is N-acetyl galactosamine o-linked to serine or threonine. The Tn immunogen is administered in the presence of about 0.2 ml to about 2 ml adjuvant. The Tn immunogen is administered at a dose ranging from about 0.1 mg to about 2 mg. The administration of the Tn immunogen according to the method of the invention can produce anti-Tn antibody with high serum titers.

BRIEF DESCRIPTION OF THE DRAWING

The patent or application file contains at least one drawing executed in color. Copies of this patent or patent application publication with color drawing(s) will be provided by the Office upon request and payment of the necessary fee.

In FIG. 1(A) the mice received carrier protein developed low serum Tn antibody titers and in FIG. 1(B) the mice received Tn immunization developed high serum antibody titers after the first immunization (621) and the antibody titers remained high after the second immunization (628).

FIGS. 5(A) to (C) show (FIG. 5A) representative Western blots and (FIG. 5B) quantitative data determined using densitometry for nuclear factor-κB (NF-κB) and (FIG. 5C) cytosol phospho-I-κBα in lung tissues. The mice treated with carrier protein and exposed to hyperoxia exhibited significantly higher nuclear NF-κB p65 and cytosol phospho-IκBα levels compared to the mice treated with carrier protein or Tn vaccine and exposed to RA (*$P<0.05$). Treatment with Tn vaccine significantly lowered the hyperoxia-induced increase in the nuclear NF-κB p65 and cytosol phospho-IκBα (*$P<0.05$).

FIG. 6A. Immunohistochemical analysis of Tn antigen in inflammatory tissues (top) and normal tissues (bottom). Tn staining in atherosclerotic aorta (left; labeled Aorta), bronchitis tissue (middle; labeled Bronchi), and periodontitis tissue (right; labeled Gingiva). Brown color represents Tn antigen expression. FIG. 6B. HGFs were treated with conditioned media from U937 cells stimulated with LPS (0, 10, 30 and 100 ng/ml; 24 hours) for 24 hours and then stained with purified rabbit anti-Tn antibody (in red) and DAPI (in blue). FIG. 6C. U937 cells were treated with LPS (0, 10, 30 and 100 ng/ml) for 24 hours, the secretions of TNF-α were analyzed by ELISA. Original magnifications (100×). Scale bar, 50 μm.

FIGS. 7A and 7B show pro-inflammatory cytokines, TNF-α and IL-6, up-regulates Tn levels in HGFs. FIG. 7A. The effect of pro-inflammatory cytokines on Tn expression in HGFs. HGFs were treated with purified TNF-α, IL-6 and IL-1β at the concentration of 0, 10, 30, and 100 ng/ml for 24 hours and then stained with purified rabbit anti-Tn antibody (in red) and DAPI (in blue). Original magnification (100×); scale bar, 50 μm. FIG. 7B. Time course analysis of Tn expressions in HGFs after TNF-α treatment. HGFs were treated with purified TNF-α at the concentration of 30 ng/ml for 4, 8, 12, 24 and 48 hours and then stained with purified rabbit anti-Tn antibody (in red) and DAPI (in blue) (Magnifications 630×; scale bar, 50 μm). The experiments were repeated at least three times.

FIGS. 8A to D show that TNF-α up-regulated Tn levels is through down-regulation of the COSMC gene in HGFs. FIG. 8A. Effect of TNF-α and demethylation agents (5-aza-dC) on mRNA expression of COSMC and T-synthase in HGFs. qPCR was used to analyze COSMC and T-synthase mRNA expression in HGFs upon TNF-α and 5-aza-dC treatment. The mRNA expression of COSMC and T-synthase was normalized to GAPDH and statistically analyzed. (*: $p<0.05$ compared with TNF-α only) Calculations of relative gene expression (normalized to GAPDH reference gene) were performed according to the ΔΔCT method. Fidelity of the PCR reaction was determined by melting temperature analysis. FIG. 8B. Western blotting was used to analyze the protein levels of Cosmc and T-synthase upon 6 and 24 hours of TNF-α treatment. FIG. 8C. and FIG. 8D. HGFs were treated with purified TNF-α for 6 or 24 hours and then immunofluorescent stained with anti-Cosmc (in red) and anti-T-synthase antibodies (in green) and DAPI (in blue). Original magnification (100×); scale bar, 50 μm.

FIG. 9A. Effect of TNF-α and demethylation agents on the methylation level of COSMC gene in HGFs. The comparison of methylation changes is in the HGFs which were treated with or without TNF-α and demethylation agents. The UCSC genome browser illustrated the orientation and the first exon of COSMC (blue bar), GC percent (black scale bar), CpG islands (green bar) and the sequencing region of bisulfite pyrosequencing (COSMC_py02, black bar). The red circle shows CG islands, and the black color displays the level of methylation.

DETAILED DESCRIPTION OF THE INVENTION

Figure 1A:
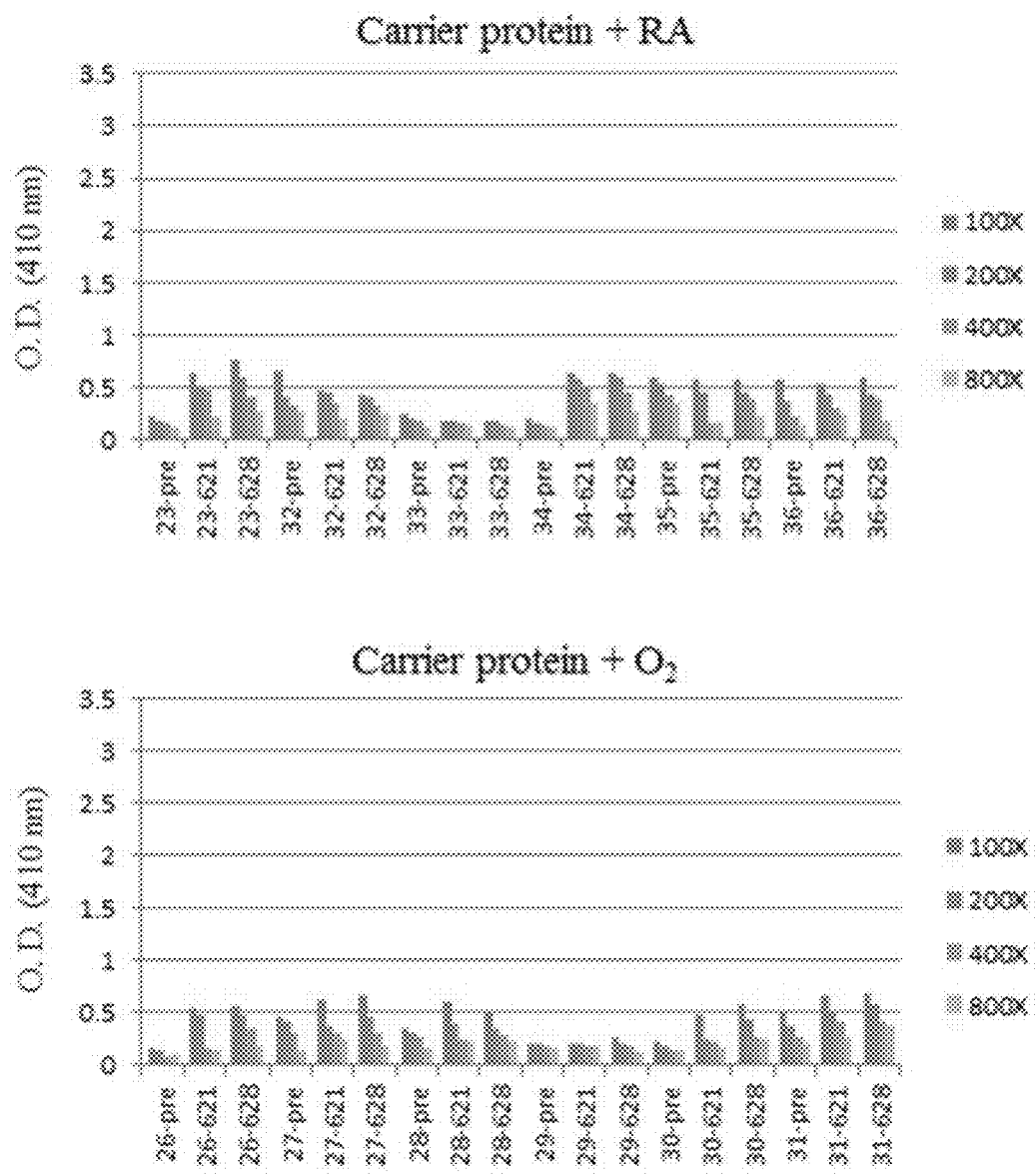
FIGS. 1(A) and (B) show serum titers of anti-Tn antibody before and after immunization. The levels of anti-Tn antibody before immunization (pre) were low in all mice.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in a different order and/or concurrently with other acts or events.

The terminology used herein is for the purpose of describing particular embodiments only and is not intended to be limiting with respect to the invention. As used herein, the singular forms "a", "an" and "the" are intended to include the plural forms as well, unless the context clearly indicates otherwise.

As used herein, the term "expression" is defined as the transcription and/or translation of a particular nucleotide sequence driven by its promoter.

As used herein, the term "promoter" is defined as a DNA sequence recognized by the synthetic machinery of the cell, or introduced synthetic machinery, required to initiate the specific transcription of a polynucleotide sequence.

As used herein, the term "antigen" or "Ag" is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

As used herein, "Tn antigen" denotes GalNAca-O-Ser/Thr, i.e. an antigen wherein the GalNAc residue is alpha-linked directly to the hydroxyl group of a serine or threonine residue of a polypeptide chain expressed intracellularly or at the cell surface.

As used herein, the term "antibody" refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies, human antibodies, and humanized antibodies As used herein, the term "polyclonal antibodies" refers to an antibody population that includes a variety of different antibodies directed to the same and/or to different epitopes within an antigen or antigens.

As used herein, the term "monoclonal antibody" refers to an antibody obtained from a population of homogenous or substantially homogeneous antibodies. The term "monoclonal" is not limited to any particular method for making the antibody. Generally, a population of monoclonal antibodies can be generated by cells, a population of cells, or a cell line.

As used herein, the terms "patient," "subject," "individual," and the like are used interchangeably, and refer to any animal, or cells thereof whether in vitro or in situ, amenable to the methods described herein. In certain non-limiting embodiments, the patient, subject or individual is a human As used herein, the term "immunoglobulin" or "Ig" is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "vaccine" refers to an immunogenic composition comprising an antigen which, when administered to a subject induces or stimulates or elicits cellular or humoral immune responses to the antigen of the vaccine. A vaccine may contain an adjuvant to produce a more robust immune response in the subject to the antigen.

As used herein, the term "adjuvant" refers to a substance used in combination with an antigen or combination of antigens to produce a more robust immune response in a subject than the antigen or combination of antigens alone.

As used herein, the phrases "stimulating an immune response", "inducing an immune response" and "eliciting an immune response" are used interchangeably unless stated otherwise and include, but are not limited to, inducing, stimulating, or eliciting a therapeutic or prophylactic effect that is mediated by the immune system of a subject.

An "effective amount" as used herein, means an amount which provides a therapeutic or prophylactic benefit.

The vaccination with Tn antigen would inhibit NF-κB activity and inhibit inflammation through the action of anti-Tn antibody induced by Tn immunization. The vaccine composition and method of the present invention can effectively treat or prevent an inflammation disease. Tn immunization increases serum anti-Tn antibody titers, while decreasing lavaged protein and cytokines. The present invention thus proposes that Tn immunization can attenuate inflammation-related disorders and organ injury. The present invention develops a vaccine composition against and treatment or prevention on inflammation and lung injury (particularly hyperoxia-induced lung injury) and progression of periodontitis. Tn immunization also decreases mean linear intercept and lung injury score. Furthermore, the improvement in lung injury is accompanied by a decrease in NF-κB activity.

In one aspect, the present invention provides a single dose vaccine, comprising about 0.1 mg to about 2 mg of a Tn immunogen per dose and an adjuvant solution in a ratio of about 0.5 to about 2 (v/v) to about 0.5 to about 2 (v/v). In one embodiment, the ratio of the Tn immunogen to the adjuvant solution is about 1 (v/v):about 1 (v/v).

In some embodiments, the dose of Tn immunogen ranges from about 0.01 mg to about 4 mg; including, for example, 0.01 mg, 0.02 mg, 0.03 mg, 0.04 mg, 0.05 mg, 0.06 mg, 0.07 mg, 0.08 mg, or 0.09 mg to about 0.1 mg; or 0.1 mg to about 1.5 mg, about 0.1 mg to about 1.2 mg, about 0.1 mg to about 1 mg, about 0.1 mg to about 0.8 mg, about 0.1 mg to about 0.5 mg, about 0.2 mg to about 1.5 mg, about 0.2 mg to about 1.2 mg, about 0.2 mg to about 1 mg, about 0.2 mg to about 0.8 mg, about 0.2 mg to about 0.5 mg, about 0.5 mg to about 2 mg, about 0.5 mg to about 1.5 mg, about 0.5 mg to about 1.2 mg, about 0.5 mg to about 1 mg, about 0.5 mg to about 0.8 mg or about 1.0 mg to about 2 mg; or about 1 mg to 3 mg; or about 1.5 mg to about 2.5 mg; or about 1.6 to about 2.4 mg; or about 1.7 mg to about 2.3 mg, or about 1.8 to about 2.2 mg, or about 1.9 to about 2.1 mg, or about 2.0 mg; or a value that falls in the range between any of the two above-recited values. The volume of the adjuvant solution ranges from about 0.1 ml to 2 ml; including for example, 0.2 ml to about 1 ml, about 0.2 ml to about 0.8 ml or about 0.2 ml to about 0.6 ml or about 0.4 ml to about 2 ml, or about 0.4 ml to about 1.6 ml, or about 0.4 ml to about 1.2 ml.

In another aspect, the present invention provides a method of inducing an immune response to treat and/or prevent an inflammation disease in a subject, comprising administering a single dose vaccine comprising about 0.1 mg to about 4 mg of a Tn immunogen per dose to the subject. In one embodiment, the single dose vaccine comprises about 0.1 mg to about 2 mg of a Tn immunogen per dose and an adjuvant solution in a ratio of about 0.5 to about 2 (v/v) to about 0.5 to about 2 (v/v).

In one aspect, the present invention provides a method of inducing an immune response to treat or prevent an inflammation disease in a subject, comprising administering about 0.1 mg to about 4 mg of a Tn immunogen per dose to the subject at least four times at biweekly intervals. In one embodiment, the method further comprises an additional immunization with about 0.1 mg to about 4 mg of the Tn immunogen one week after the fourth immunization. In one embodiment, the additional immunization can be conducted one or more times after the last immunization. In one embodiment, the single dose vaccine comprises about 0.1 mg to about 2 mg of a Tn immunogen per dose and an adjuvant solution in a ratio of about 0.5 to about 2 (v/v) to about 0.5 to about 2 (v/v). In one embodiment, the single dose vaccine comprises about 0.1 mg to about 3 mg of a Tn immunogen per dose and an adjuvant solution in a ratio of about 0.5 to about 2 (v/v) to about 0.5 to about 2 (v/v). In one embodiment, the single dose vaccine comprises about 0.1 mg to about 4 mg of a Tn immunogen per dose and an adjuvant solution in a ratio of about 0.5 to about 2 (v/v) to about 0.5 to about 2 (v/v). In one embodiment, the single dose vaccine comprises about 0.1 mg to about 2.5 mg of a Tn immunogen per dose and an adjuvant solution in a ratio of about 0.5 to about 2 (v/v) to about 0.5 to about 2 (v/v). In one embodiment, the single dose vaccine comprises about 0.1 mg to about 1.5 mg of a Tn immunogen per dose and an adjuvant solution in a ratio of about 0.5 to about 2 (v/v) to about 0.5 to about 2 (v/v).

The administration of the Tn immunogen according to the method of the invention can produce anti-Tn antibody with high serum titers than the titer of the control. In one embodiment, the serum titer of the produced anti-Tn antibody is at least about 2, 2.5, 3, 3.5, 4, 4.5, 5, 5.5 or 6 or more (or a value that falls in the range between any of the two above-recited numbers) folds higher than the titer of the control. The "control" used herein refers to carrier polypeptide.

In one embodiment, the Tn immunization reduces interleukine-6 (IL-6) and TNF-α levels or decreases NF-κB activity in a cell or a subject.

In one embodiment, the cell or the subject has an elevated Tn expression. In a further embodiment, the Tn expression is upregulated by TNF-α and IL-6. In another further embodiment, the elevated Tn levels is commonly regulated by the cytokine-Cosmc signaling axis.

In one embodiment, the inflammation disease is progression of periodontitis, organ injury or organ fibrosis. In a further embodiment, the organ injury is lung injury, renal injury or liver injury. In a further embodiment, the lung injury is hyperoxia-induced lung injury. In a further embodiment, the organ fibrosis is lung fibrosis, liver fibrosis or renal fibrosis.

In one embodiment, the method further comprises a step of having an additional immunization one week after the fourth immunization.

In some embodiments, the Tn immunogen can be conjugated with a carrier polypeptide. The Tn immunogen and the carrier polypeptide are at a weight ratio of about 3 to about 8:about 1; preferably, the weight ratio is about 5:about 1. In some embodiments, the polypeptide includes, but is not limited to, an antigen presenting cell (APC) binding domain and a cysteine-rich domain. In some embodiments, the APC binding domain is an immunoglobulin (Ig) Fc fragment or a receptor-binding domain of a toxin. In a further embodiment, the APC binding domain is a receptor-binding domain of *Pseudomonas* exotoxin A, tetanus toxin, or cholera toxin. In a further embodiment, the APC binding domain is a Fc fragment of a human Ig. In some other embodiments, the cysteine-rich domain contains a fragment of 10 amino acid residues, at least 3 of which are cysteine residues. In another further embodiment, the cysteine-rich domain contains 6 cysteine residues. Preferably, the cysteine-rich domain has the amino acid sequence of Pro-Cys-Cys-Gly-Cys-Cys-Gly-Cys-Gly-Cys (SEQ ID NO: 2). In another further embodiment, the cysteine-rich domain contains 2 to 30 repeats of the amino acid sequence. Preferably, the cysteine-rich domain contains 7 repeats of the amino acid sequence. In another embodiment, the Tn is linked to the cysteine residues via a linker (such as a linker containing a maleimide functional group; for example, N-maleimide or N-succinimidyl-6-maleimidocaproate). In another further embodiment, the Tn immunogen conjugated with a carrier polypeptide is Fc fragment-7 repeats of Pro-Cys-Cys-Gly-Cys-Cys-Gly-Cys-Gly-Cys (SEQ ID NO: 2)-Tn. Preferably, the Tn immunogen conjugated with a carrier polypeptide is Fc fragment-7 repeats of Pro-Cys-Cys-Gly-Cys-Cys-Gly-Cys-Gly-Cys (SEQ ID NO: 2)-N-maleimide-Tn or Fc fragment-7 repeats of Pro-Cys-Cys-Gly-Cys-Cys-Gly-Cys-Gly-Cys (SEQ ID NO: 2)-N-succinimidyl-6-maleimidocaproate-Tn.

In one embodiment, the Tn immunogen is N-acetyl galactosamine o-linked to serine or threonine, which has the following structure.

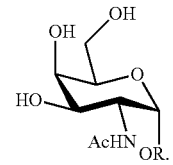

R is serine or threonine

In one embodiment, the Tn immunogen is administered in the presence of 0.2 ml to 2 ml adjuvant. In some embodiments, the adjuvant is aluminum hydroxide, aluminum phosphate, calcium phosphate hydroxide, killed bacteria *Bordetella pertussis, Mycobacterium bovis*, toxoids, squalene, Quil A, saponins, IL-1, IL-2, IL-12, Freund's complete adjuvant or Freund's incomplete adjuvant. In a further embodiment, the adjuvant is aluminum phosphate.

Vaccine compositions comprising the Tn immunogen of the invention may be administered to a subject already suffering from inflammation. In therapeutic applications, compositions are administered to a patient in an amount sufficient to elicit an effective immune response to the present antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally the range for the initial immunization (that is for therapeutic or prophylactic administration) can be from about 0.1 mg to 4 mg of Tn immunogen for a subject, followed by boosting dosage from about 0.1 mg to 4 mg of Tn immunogen pursuant to a boosting regimen described herein. In one embodiment, the initial immunization is from about 0.1 mg to about 2 mg of Tn immunogen for a subject, followed by boosting dosage from about 0.1 mg to about 2 mg of Tn immunogen The vaccine compositions are intended for parenteral, topical, nasal, oral or local administration. Preferably, the pharmaceutical compositions are administered parenterally, e.g., intravenously, subcutaneously, intradermally, or intramuscularly. Preferably, the vaccine is administered intramuscularly. The invention provides compositions for parenteral administration which comprise a solution of the vaccine compositions dissolved or suspended in an acceptable carrier, preferably an aqueous carrier. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

By way of example, and not of limitation, examples of the present invention shall now be given.

EXAMPLES

Materials and Methods
Animal Model

Five-week-old female C57BL/6NCrlBltw mice were obtained from BioLASCO Taiwan Co., Ltd and were maintained in a pathogen free facility. Animals were kept at approximately 25° C. and pelleted food and water were available ad libitum throughout the experiment. The study protocol was approved by the Institutional Animal Care and Use Committee of Taipei Medical University (LAC-2016-0047). As described herein, an animal model was used as a demonstration of vaccine efficacy. Human equivalent dosage information can be readily calculated by those of skill in the art and is described in, for example, Herati et al, *Cold Springs Harbor Perspectives in Biology, Mar.* 17, 2017.
Preparation of Tn Vaccine Tn vaccine was prepared by conjugating Tn to a carrier protein as described in previous study (H. L. Chiang, C. Y. Lin, F. D. Jan, Y. S. Lin, C. T. Hsu, J. Whang-Peng, L. F. Liu, S. Nieh, C. C. Lin, J. Hwang, *A novel synthetic bipartite carrier protein for developing glycotope-based vaccines. Vaccine* 30 (2012) 7573-7581). Tn was conjugated to ratFc (Cys42)Histag2 or GST(Cys6)Histag2 at a glycotope/carrier protein weight ratio of 5 to 1. Conjugation was performed in buffer containing 20 mM sodium phosphate, pH 7.9, 8 M urea, 500 mM imidazole, and 0.2 mM TCEP. After 48 hours, conjugate was refolded against phosphate-buffered saline (PBS) with 0.2 mM TCEP. GST(Cys6) was dialyzed against PBS with 0.2 mM TCEP. Different glycotopes and Linker (N-Succinimidyl-6-Maleimidocaproate) were conjugated to GST(Cys6) at 4° C. for 48 hours.
Experimental Groups of Mice Five-week-old female C57BL/6NCrlBltw mice were subcutaneously immunized with Tn vaccine at a dose of 20 µg or carrier protein (10 µg of mFc(Cys42-Tn)Histag2) in the presence of adjuvant in 100 µl for four times at biweekly intervals and one additional immunization at one week later after the fourth immunization. Blood was withdrawn from facial vein for anti-Tn antibody titer measurement using enzyme-linked immunosorbent assay (ELISA) on days 0, 42, and 49. Four days after the last immunization, mice were exposed to room air (RA) or oxygen-enriched atmosphere (100% $O_2$) for up to 96 hours. Oxygen exposures was carried out in a transparent 60×50×40-cm Plexiglas chamber into which oxygen was continuously delivered at 4 l/min and oxygen levels were monitored with a ProOx Model 110 monitor (NexBiOxy, Hsinchu, Taiwan) and humidity was checked daily and the value was 60-80%. We obtained four study groups as follows: carrier protein+RA (n=6), Tn vaccine+RA (n=6), carrier protein+$O_2$ (n=6), and Tn vaccine+$O_2$ (n=5). Mice were deeply anesthetized with an overdose of isoflurane after 96 hours $O_2$ treatment. Lung was lavaged with 0.6 ml 0.9% saline at 4° C. which washed in and out of the lungs three times and then recovered. This washing procedure was repeated two more times for each animal, with the three washes being pooled, and the total volume recorded. The right lung was ligated, and left lung was fixed by tracheal instillation of 4% buffered paraformaldehyde at a pressure of 25 cm $H_2O$ for 10 min after bronchoalveolar lavage.
Analysis the Levels of Serum Anti-Tn Antibody by ELISA GST(Cys6-Tn) was coated on 96-well flat-bottomed plates (Falcon Labware, Lincoln Park, N.J., USA) at a concentration of 1.5 µg/ml. Various diluted antiserum was add to each coated well. After incubating at 37° C. for 2 hours, the wells were washed with PBS three times. Subsequently, peroxidase-conjugated anti-human immunobulin was added, and the plates were incubated at 37° C. for 1 hour. The substrate solution contained 0.54 mg/ml 2,2'-azino-bis(3-ethylbenzthiazoline-6-sulfonic acid) and 0.01% $H_2O_2$, and 0.1M citric acid (pH 4.2). Absorbance was read at 410 nm.
Bronchoalveolar Lavage Fluid Protein and Cytokines Analysis Total protein concentration in bronchoalveolar lavage fluid (BALF) was measured with a bicinchoninic acid assay (Pierce Chemical, Rockford, Ill., USA). The levels of IL-6 and TNF-α in the BALF were determined using the ELISA kit (Cloud-Clone Corp., Houston, Tex., USA). The data were expressed in mg/ml and pg/ml, respectively.
Western Blot Analysis of NF-κB Subcellular protein fractionation was done using the Subcellular Protein Fractionation Kit for Tissue (Thermo Scientific, Melbourne, VIC, Australia, ca t#87790). Nuclear protein extracts were used to detect the NF-κB p65 (SC-372, Santa Cruz Biotechnologies, Santa Cruz, Calif., USA) subunit and PCNA (SC-7907); cytoplasmic protein extracts were used to detect IκB-α (SC-1643) and β-actin (SC-47778). Protein concentrations were determined with a bicinchoninic acid protein assay kit. Proteins were separated on a 12% sodium dodecyl sulfate polyacrylamide gel and transferred onto polyvinylidene difluoride membranes, and the membranes were blocked in 5% skim milk at room temperature for 1 hour. The membranes were incubated at 4° C. overnight with antibodies. Subsequently, the membranes were incubated with HRP-conjugated secondary antibody at room temperature for 1 hour. The signal was visualized by enhanced chemiluminescence reagents according to the manufacturer's protocol. Antibodies to β-actin and PCNA were used as internal controls of nuclear and cytosolic protein loading, respectively. All blotting experiments were performed at least three times with different mice.

Lung Morphometry

To standardize analysis, sections are taken from the right middle lobe of the right lung. Five-μm lung tissue sections are stained with hematoxylin and eosin and assessed for lung morphometry. Mean linear intercept (MLI), an indicator of mean alveolar diameter, is assessed in 10 nonoverlapping fields [18].

Histology

Lung tissues were fixed in 4% paraformaldehyde in phosphate buffer, embedded in paraffin, stained with hematoxylin and eosin, and examined by a pathologist who was blinded to the protocol and experimental groups. Lung injury was scored according to the following four criteria: 1) alveolar congestion, 2) hemorrhage, 3) infiltration of neutrophils in the air space or vessel wall, and 4) thickness of the alveolar wall. Each item was graded according to a five-point scale as follows: 0 for minimal (little) damage, 1 for mild damage, 2 for moderate damage, 3 for severe damage, and 4 for maximal damage [19].

Immunohistochemistry of NF-κB

After a routine deparaffinization step, heat-induced epitope retrieval was performed by immersing the slides in 0.01 mol/L sodium citrate buffer (pH 6.0). To block the endogenous peroxidase activity and nonspecific antibody binding, sections were first preincubated for 1 hour at room temperature in 0.1 mol/L PBS containing 10% normal goat serum and 0.3% $H_2O_2$ before incubating for 20 hours at 4° C. with the rabbit polyclonal anti-NF-κB P65 (1:50 dilution; Abcam Inc., Cambridge, Mass., USA) as primary antibody. The sections were then treated for 1 hour at room temperature with biotinylated goat anti-rabbit IgG (1:200, Vector, Calif., USA). This was followed by reaction with the reagents from an ABC kit (Avidin-Biotin Complex, Vector, Calif., USA) according to the manufacturer's recommendations, and the reaction products were visualized by diaminobenzidine substrate kit (Vector, Calif., USA). All immunostained sections were viewed and photographed by Olympus BX 43.

Statistical Analysis

All data are presented as mean±SD. Statistical analyses were performed using one-way analysis of variance with a Tukey post hoc test for multiple group comparisons. Differences were considered statistically significant when $P<0.05$.

EXAMPLES

Example 1 Serum Titers of Anti-Tn Antibody

Figure 1B:
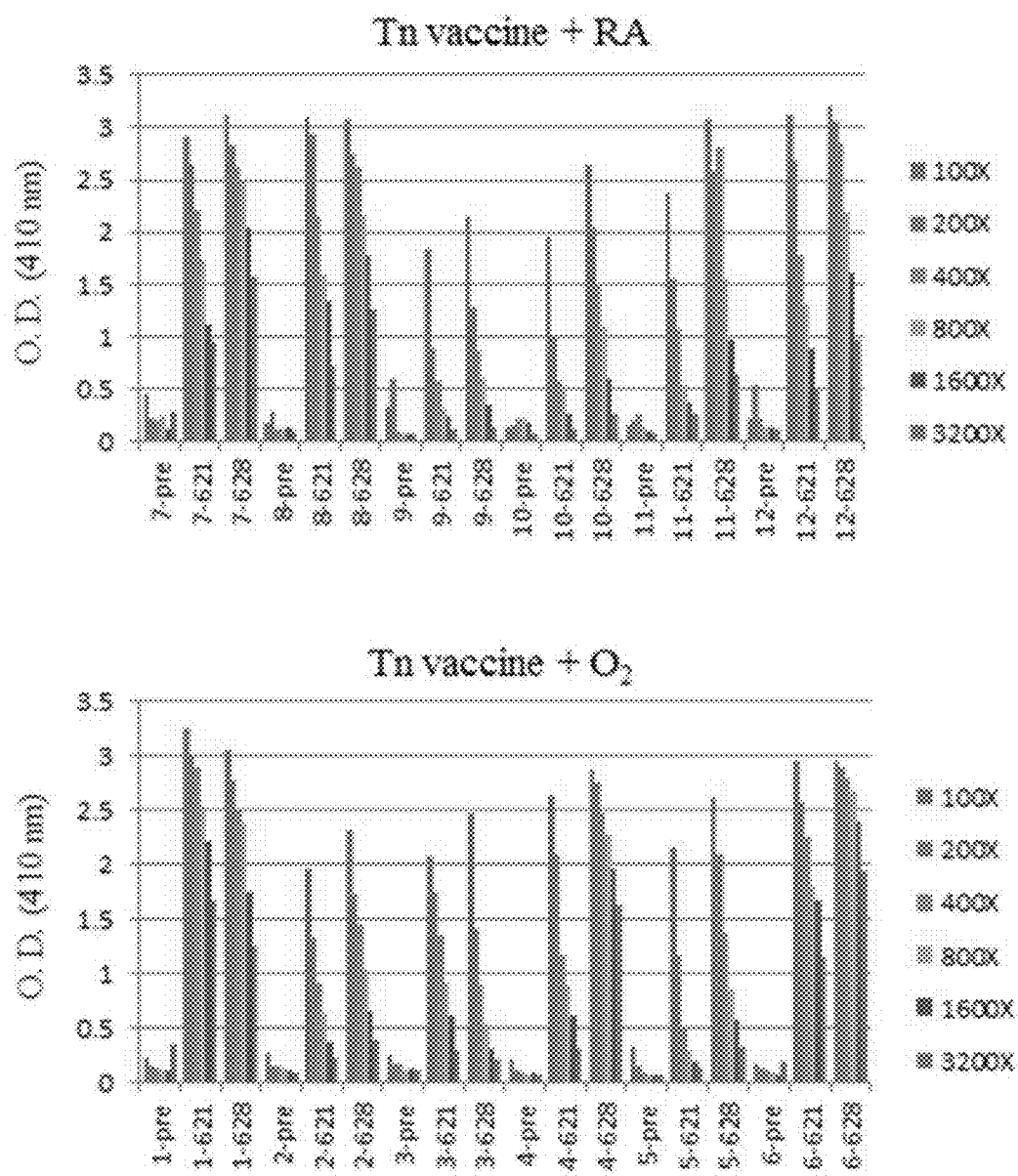

The levels of anti-Tn antibody were low in all the mice before immunization and we count it as background (FIG. 1). The mice that received carrier polypeptide (i.e., Fc fragment-7 repeats of Pro-Cys-Cys-Gly-Cys-Cys-Gly-Cys-Gly-Cys-N-succinimidyl-6-maleimidocaproate) and were housed in room air or exposed to hyperoxia showed background serum anti-Tn antibody levels (FIG. 1A), while mice received Tn vaccination developed high serum anti-Tn antibody titers after Tn vaccination and anti-Tn antibody levels remained high after several months of vaccination (FIG. 1B).

Example 2 Survival and Body Weight

Figure 2:
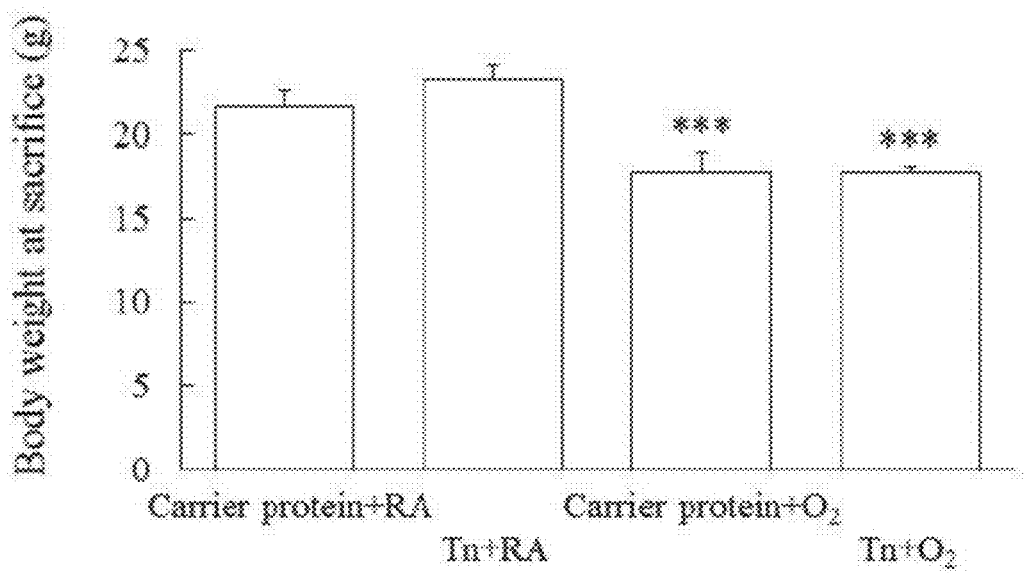
FIG. 2 shows body weight at sacrifice. The mice exposed to the room air and hyperoxia all survived. The mice reared in $O_2$-enrich atmosphere exhibited significantly lower body weights than mice reared in room air (RA) at sacrifice (***$P<0.001$).

The mice exposed to room air or hyperoxia all survived throughout the study period. The mice exposed to hyperoxia exhibited significantly lower body weights at sacrifice than those reared in room air (FIG. 2).

Example 3 Bronchoalveolar Lavage Fluid Protein and Cytokines Analysis

Figure 3A:
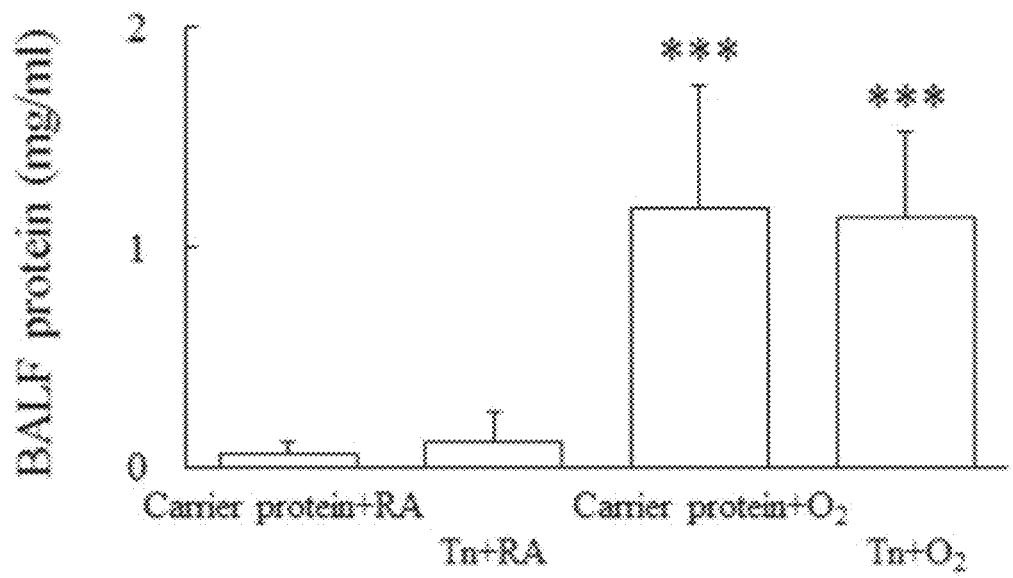
FIGS. 3A to C show bronchoalveolar lavage fluid (BALF) protein and cytokines levels. (A, B) The mice treated with carrier protein or Tn vaccine and exposed to hyperoxia exhibited significantly higher total protein and IL-6 levels in BALF than those exposed to room air (RA) ($P<0.01$ and *$P<0.001$). Tn immunization significantly lowered the hyperoxia-induced increase in the IL-6 level (*$P<0.001$). (C) The mice treated with carrier protein and exposed to hyperoxia exhibited a significantly higher TNF-α level in BALF than those exposed to RA ($P<0.01$). Tn immunization lowered the hyperoxia-induced increase in the TNF-α level.
Figure 3B:
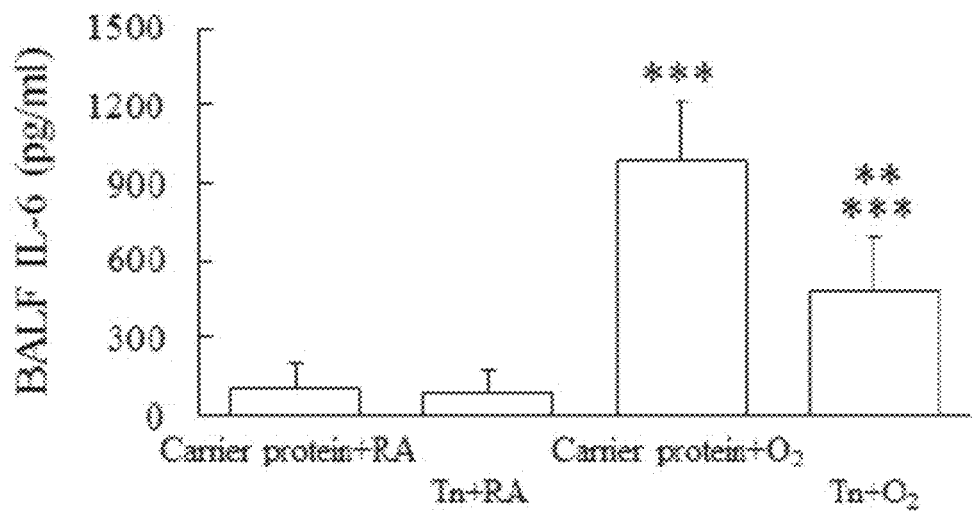
Figure 3C:
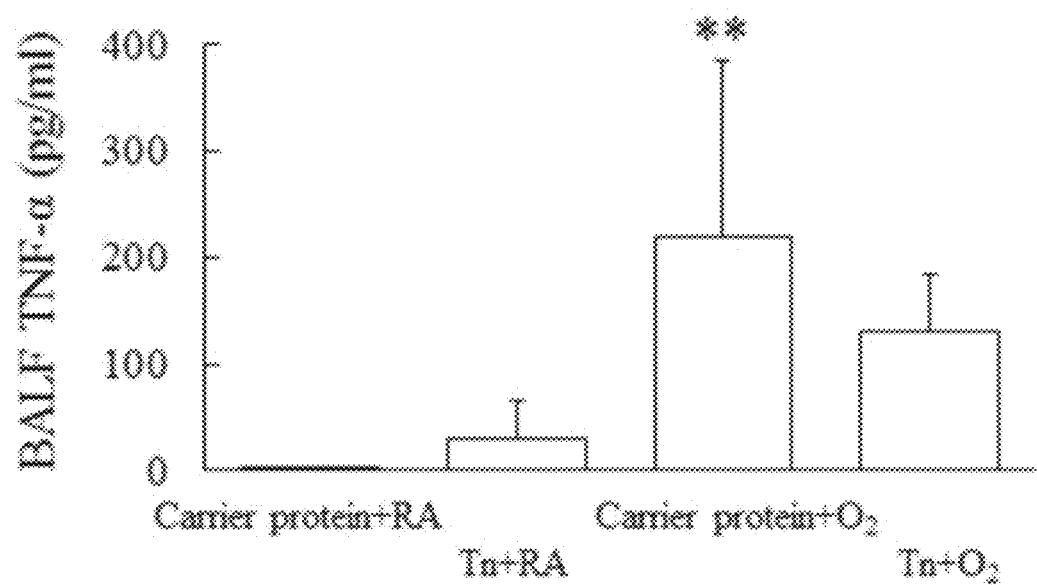

The mice treated with carrier protein, followed by exposure to hyperoxia exhibited significantly higher total protein and IL-6 levels in BALF than those exposed to room air (FIGS. 3A and B). On the other hand, the mice treated with Tn vaccine and exposed to hyperoxia exhibited a significantly lower IL-6 level in BALF than those treated with carrier protein (FIG. 3B). The mice treated with carrier protein and exposed to hyperoxia exhibited a significantly higher TNF-α level in BALF than those exposed to RA (FIG. 3C). The mice treated with Tn vaccine and exposed to hyperoxia exhibited a lower TNF-α level in BALF. However, the difference did not reach significance.

Example 4 Histology Results

Figure 4A:
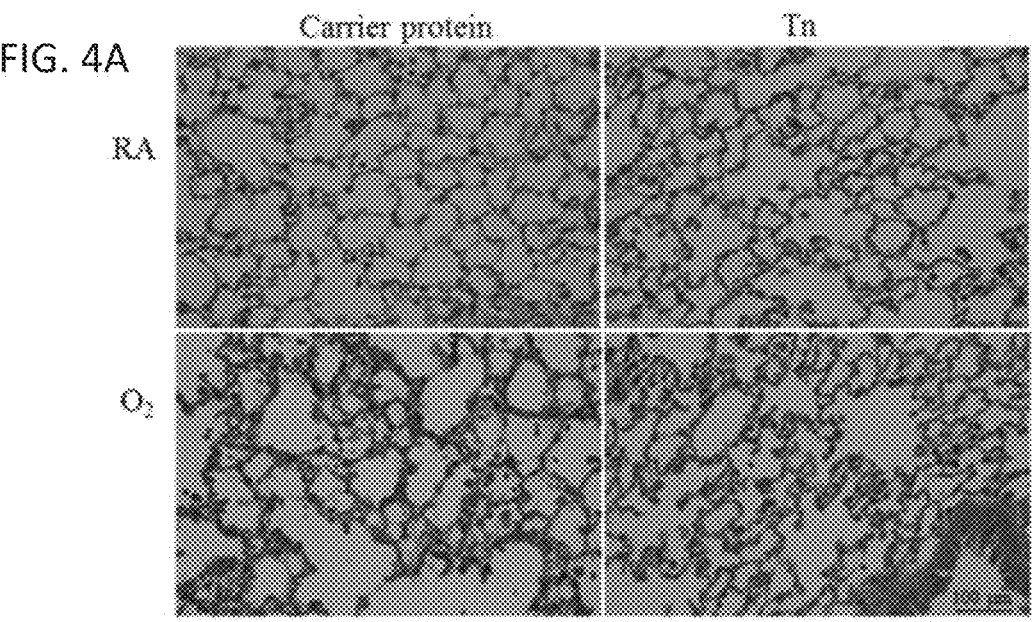
FIGS. 4(A) to (C) show (A) representative histology, (B) lung injury score, and (C) mean linear intercept (MLI) in mice treated with carrier protein or Tn vaccine and exposed to RA or hyperoxia. The mice treated with carrier protein and exposed to hyperoxia exhibited a significantly higher lung injury score and MLI compared to the mice treated with carrier protein or Tn vaccine and exposed to RA (*$P<0.001$). Tn immunization significantly lowered the hyperoxia-induced increase in the lung injury score and MLI (*$P<0.001$).
Figure 4B:
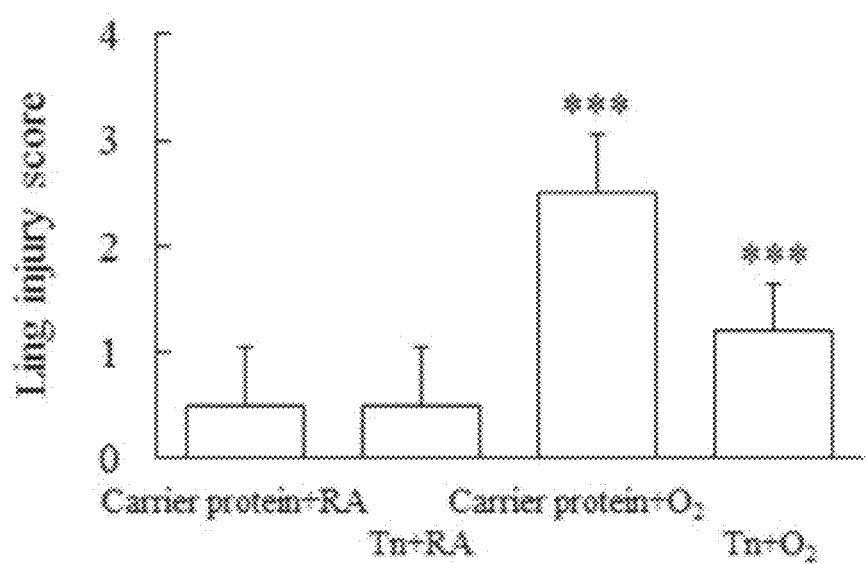
Figure 4C:
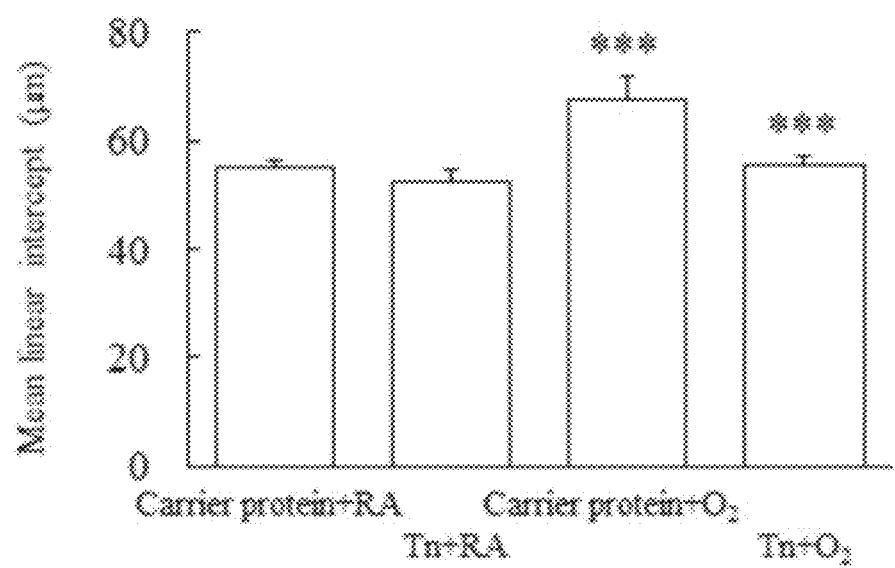

Representative lung sections stained with hematoxylin and eosin from mice exposed to RA and hyperoxia are presented in FIG. 4A. Hyperoxia resulted in inflammatory cells infiltration and simplification of the lung parenchyma, as indicated by greater linear intercept. The mice treated with carrier protein and exposed to hyperoxia exhibited a significantly higher lung injury score and MLI compared to the mice treated with carrier protein or Tn vaccine and exposed to RA (FIGS. 4B and 4C). Treatment with Tn vaccine significantly decreased the hyperoxia-induced increase in the lung injury score and MLI.

Example 5 Immunohistochemistry of NF-κB

Figure 5A:
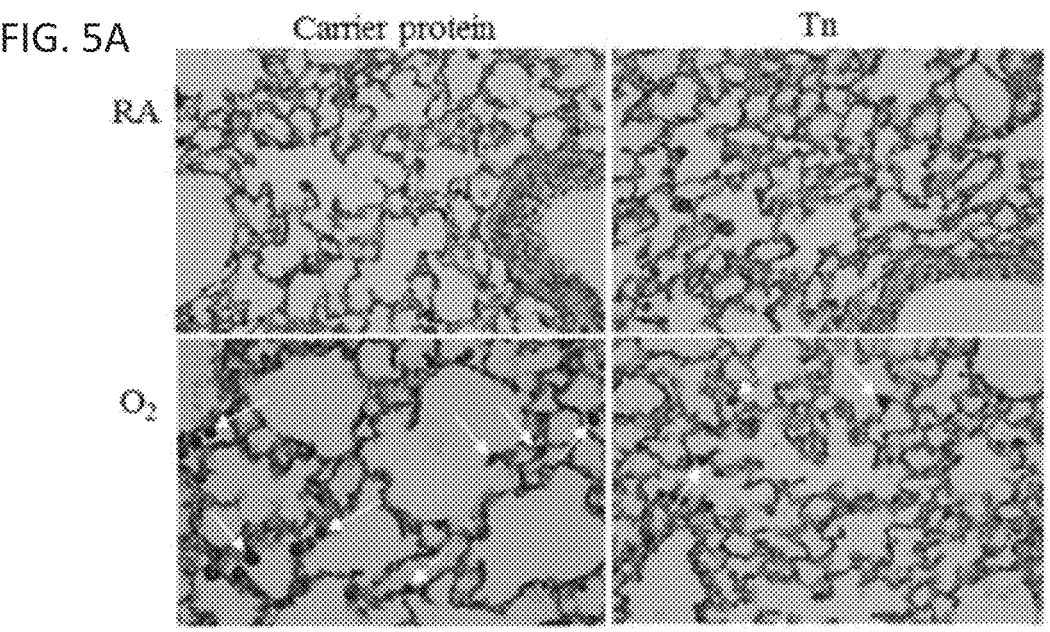

The immunohistochemical staining of NFκB was found primarily in the cytoplasm of alveolar macrophages, but the immunoreactivity was also displayed in the nuclei of alveolar macrophage and small number of alveolar epithelial cells (FIG. 5A). The lung of the hyperoxia group immunized with carrier protein exhibited more intense NFκB immunoreactivity than the control and Tn-treated hyperoxia groups.

Example 6 Western Blot Analysis for NF-kB and IkBα

Figure 5B:
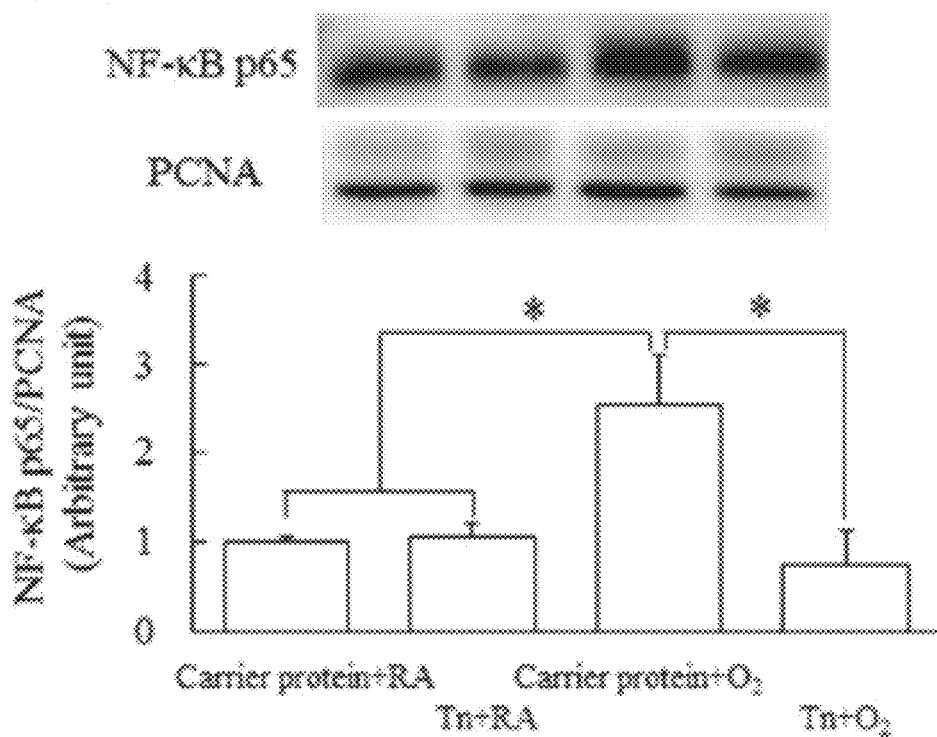

The mice treated with carrier protein and exposed to hyperoxia exhibited a significantly higher nuclear NF-κB p65 and cytosol phospho-IkBα levels compared to the mice treated with carrier protein or Tn vaccine and exposed to RA (FIGS. 5B and 5C). The group of rats treated with Tn vaccine exhibited significantly levels of NFκB p65 and cytosol phospho-IkBα even in the hyperoxia-treated rats.

Example 7 Elevated Tn Levels in Inflammatory Tissues and Cells

Figure 6A:
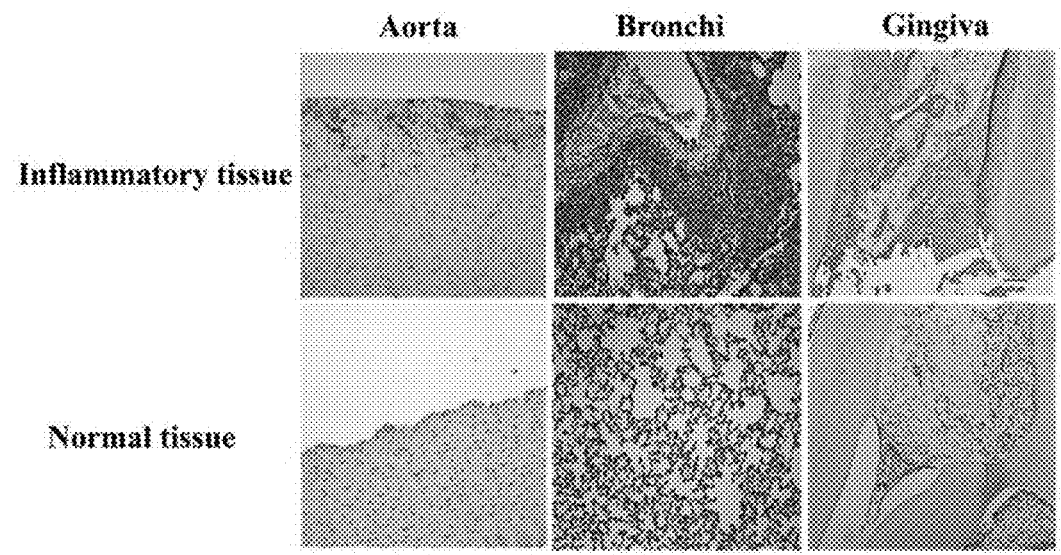
FIGS. 6A to C show that Tn levels is up-regulated in inflammatory tissues and cells.
Figure 6B:
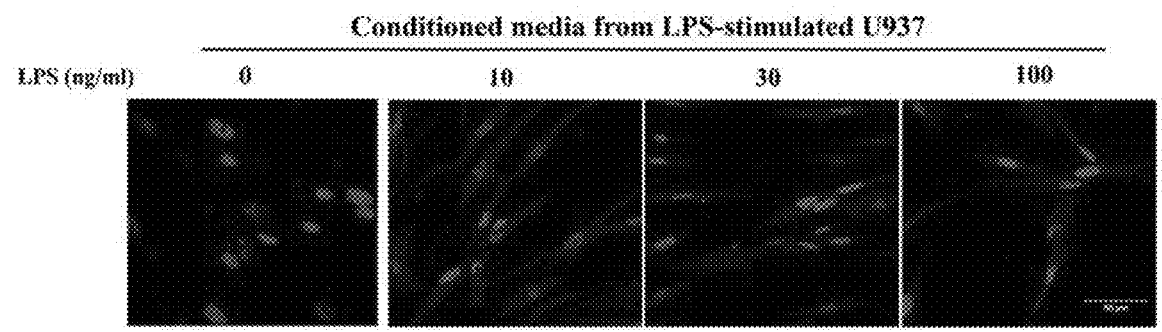
Figure 6D:
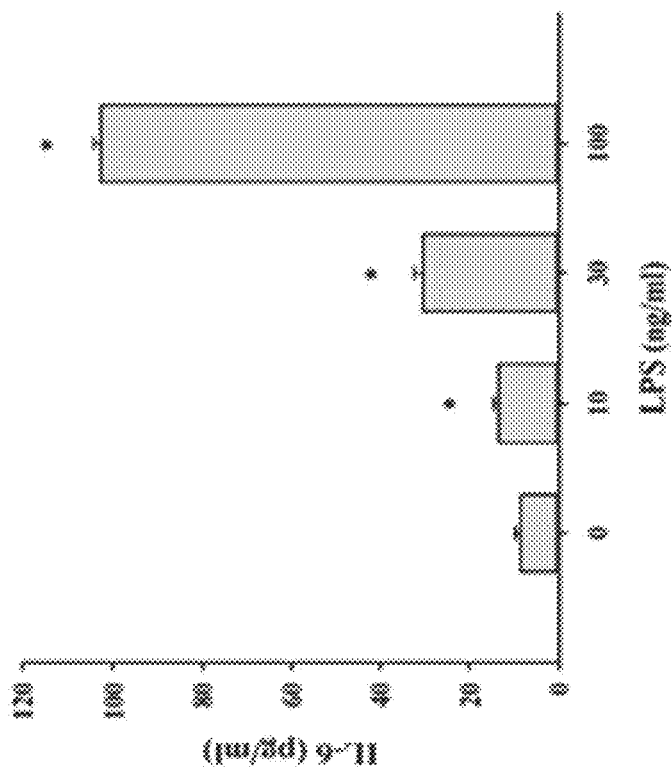
FIG. 6D. U937 cells were treated with LPS (0, 10, 30 and 100 ng/ml) for 24 hours, the secretions of IL-6 were analyzed by ELISA. Original magnifications (100×). Scale bar, 50 μm.
Figure 6C:
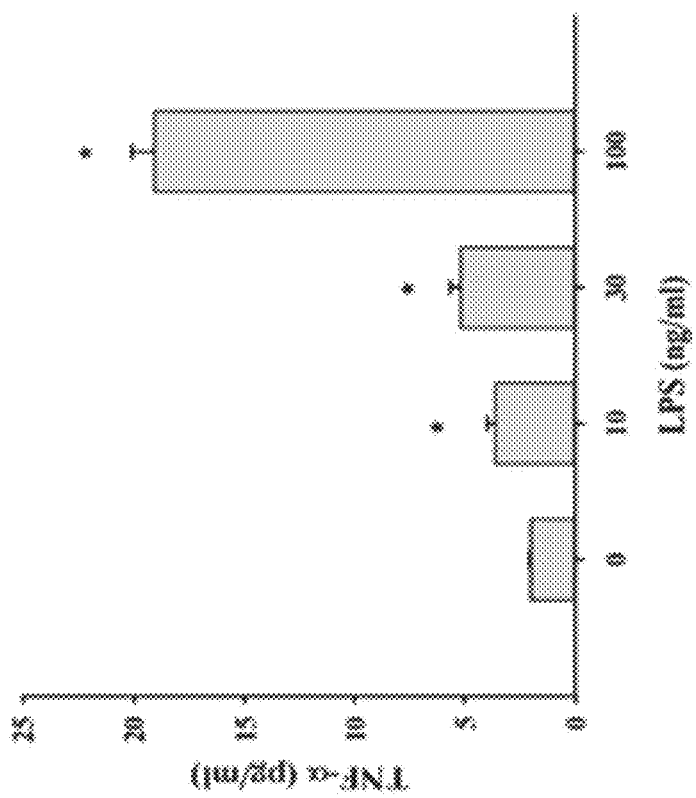
Figure 6E:
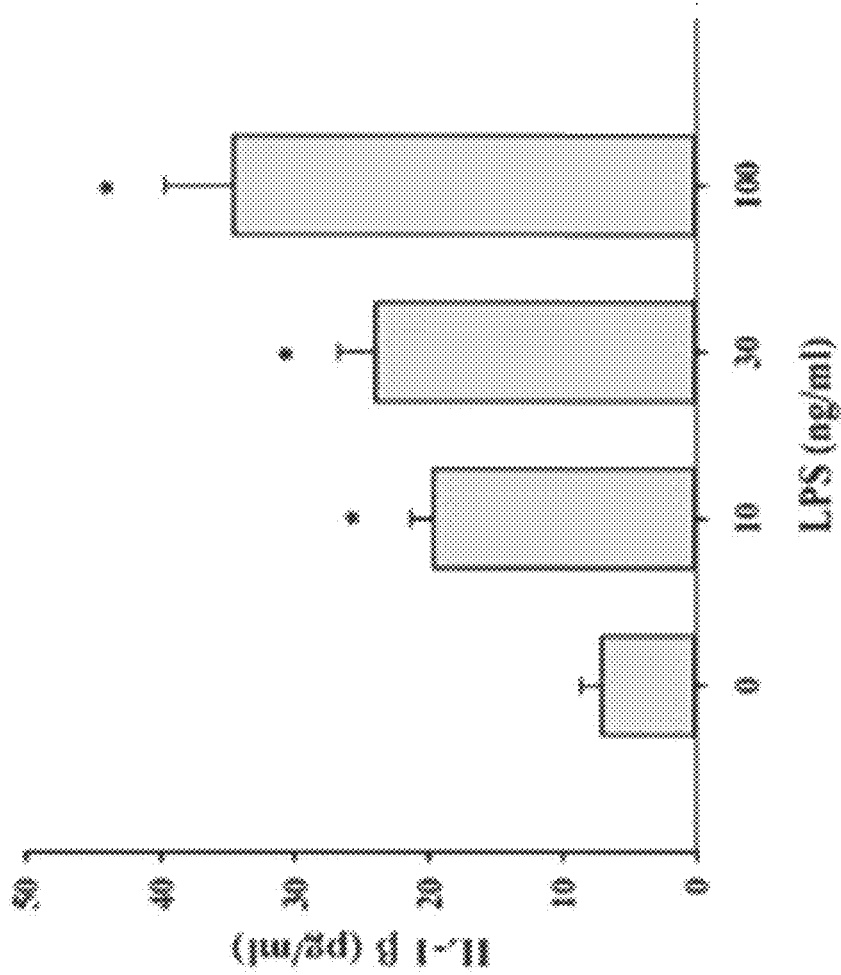
FIG. 6E. U937 cells were treated with LPS (0, 10, 30 and 100 ng/ml) for 24 hours, the secretions of IL-1β were analyzed by ELISA. Original magnifications (100×). Scale bar, 50 μm.

To examine whether elevated Tn levels are associated with inflammation, Tn levels were measured in inflammatory tissues using immunohistochemistry (IHC). A significant increase in Tn levels was observed in tissues of atherosclerosis, bronchitis and periodontitis but not in their corresponding normal tissues (FIG. 6A). To investigate the possible regulation of Tn levels by inflammatory cytokines, conditioned media from monocyte U937 cells stimulated with LPS were used. Tn levels in human gingival fibroblasts (HGFs) replenished with one-day conditioned media from LPS-stimulated U937 cells were observed to increase in an LPS-dose-dependent manner (FIG. 6B). The secretion of inflammatory cytokines (ex: TNF-α, IL-6, and IL-1β) was significantly higher in conditioned media from U937 cells treated with LPS (10, 30, or 100 ng/ml) for 24 hours compared with media from U937 cells cultured without LPS (FIG. 6C).

Example 8 TNF-α and IL-6 Up-Regulate Tn Expression in HGFs

Figure 7B:
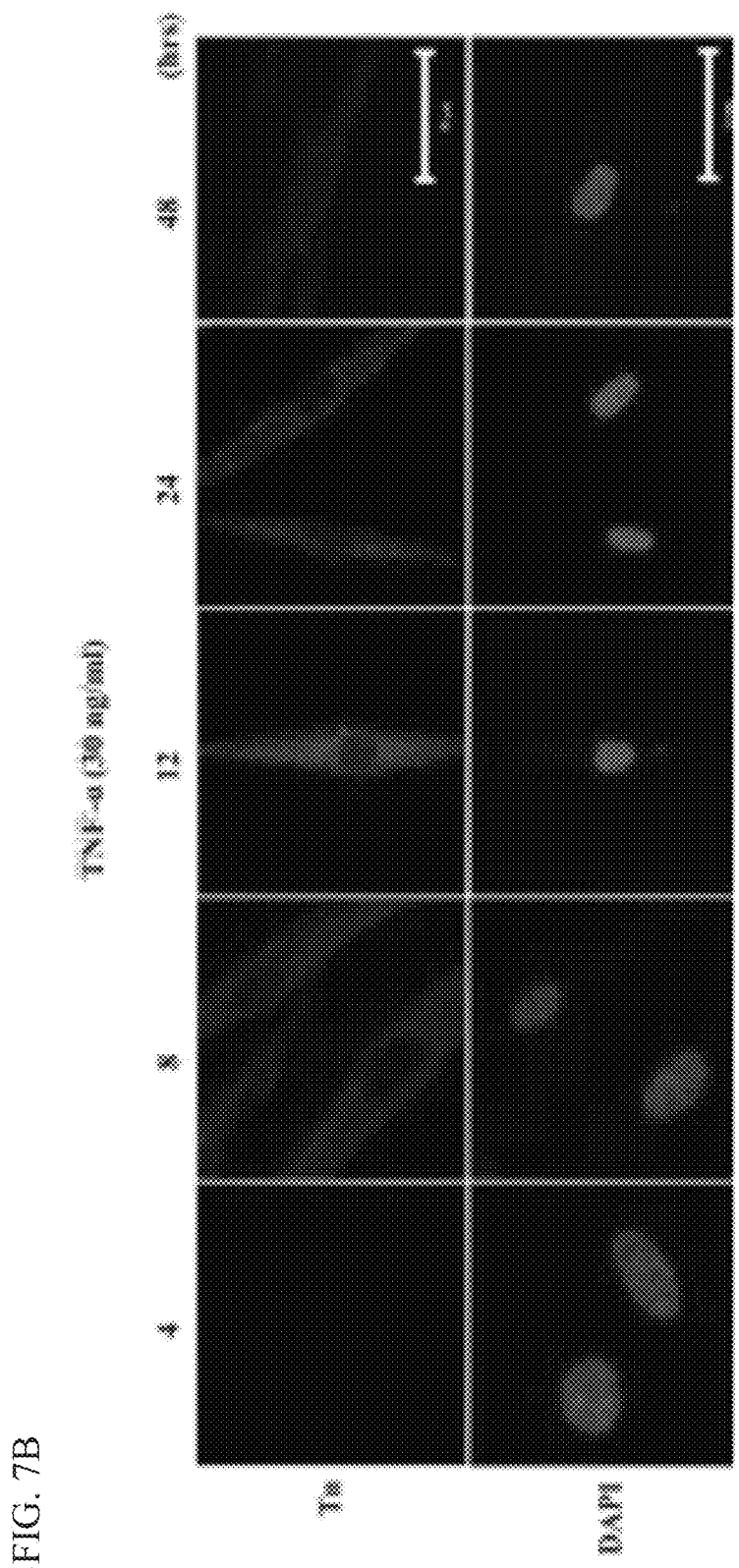

To determine whether cytokine(s) can elevate Tn levels, HGFs were treated with various amounts of purified cytokines. As shown in FIG. 7A, Tn levels in HGFs were most responsive to TNF-α, moderately responsive to IL-6, and not responsive to IL-1β, even at a concentration of 100 ng/ml under the experimental conditions. Elevation of Tn by TNF-α (30 ng/ml) was shown to be time dependent. Tn levels in HGFs were essentially unchanged upon 4 hrs of TNF-α treatment. Gradual increase in Tn levels was observed between 8 to 12 hrs. The level of Tn gradually decreased after 24 hours of TNF-α treatment and markedly decreased after 48 hours of TNF-α treatment (FIG. 7B).

Figure 8A:
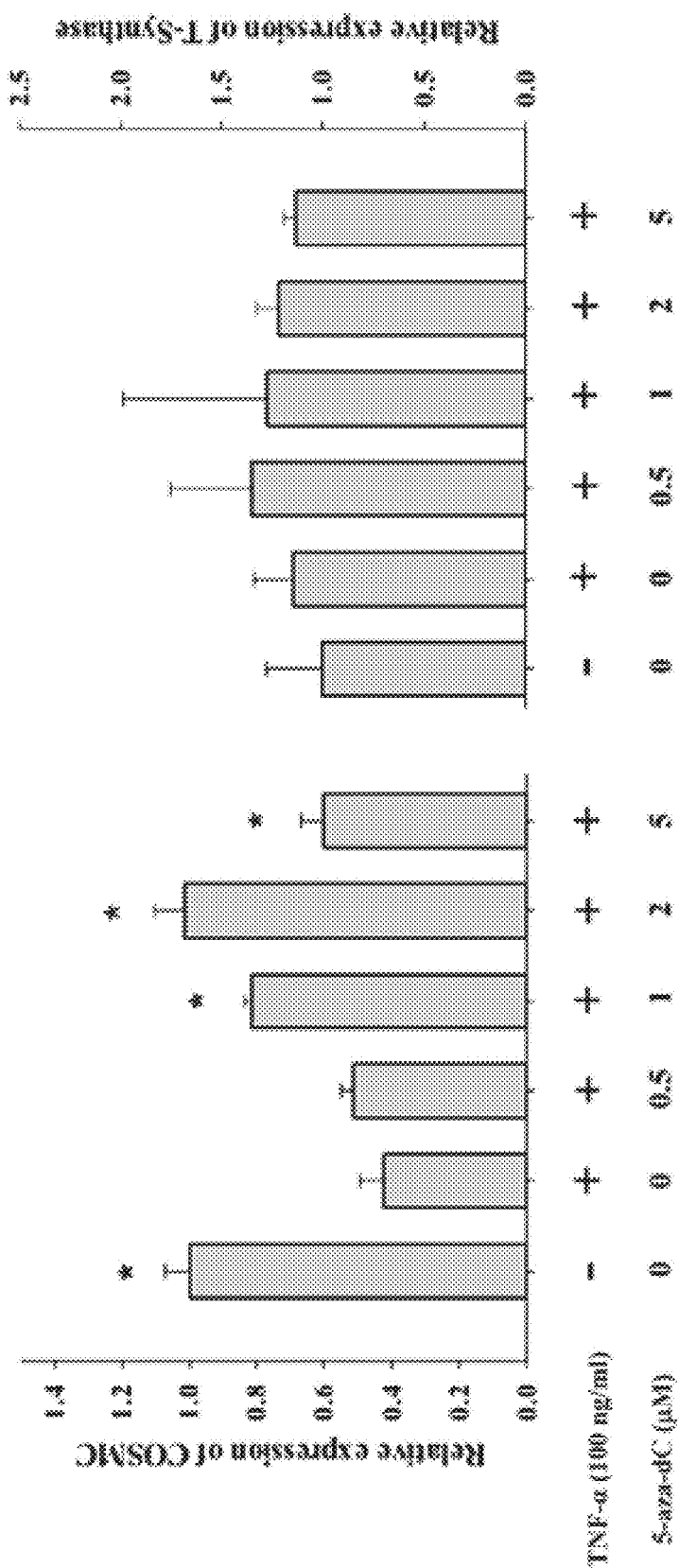
Figure 8B:
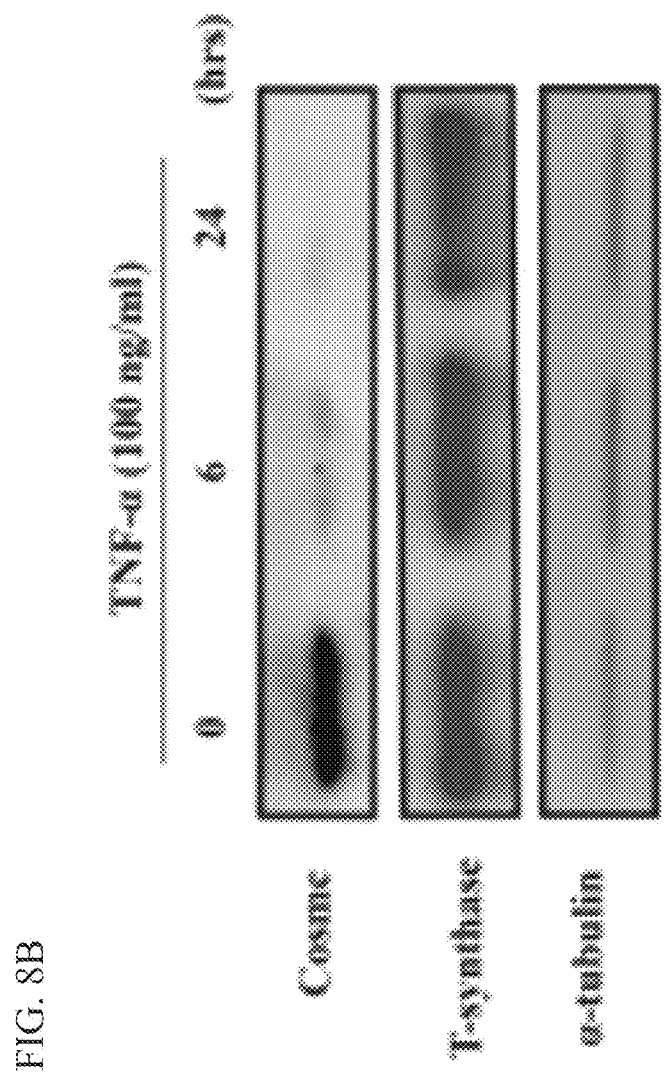
Figure 8D:
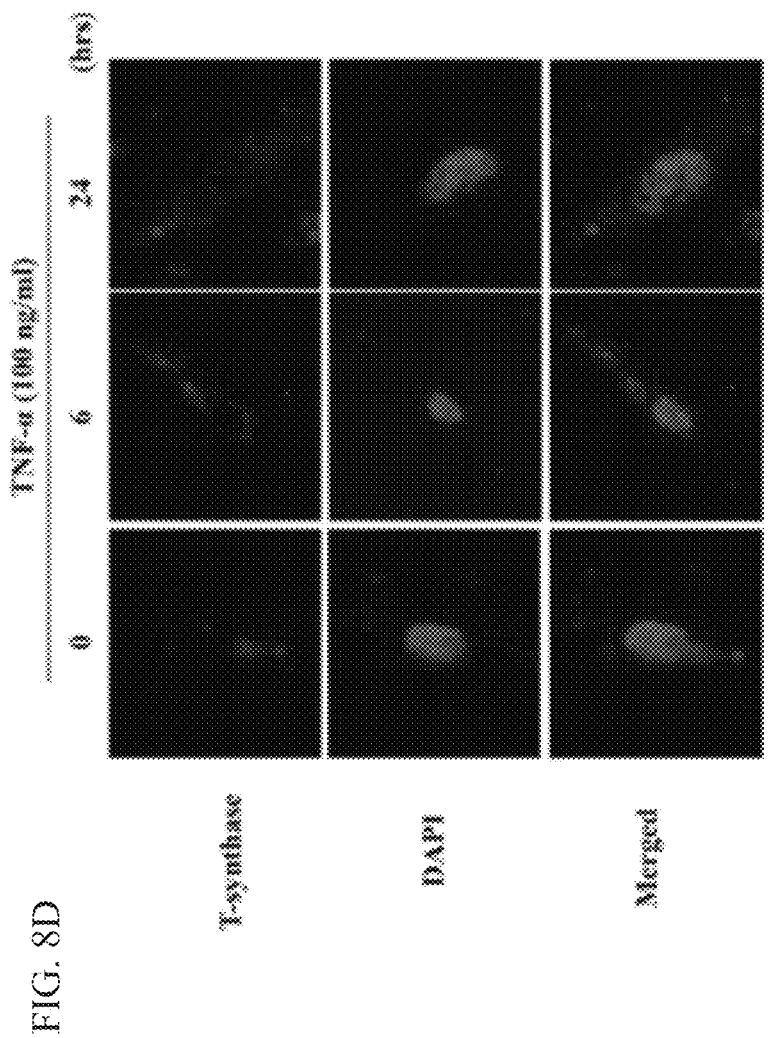
Figure 9A:
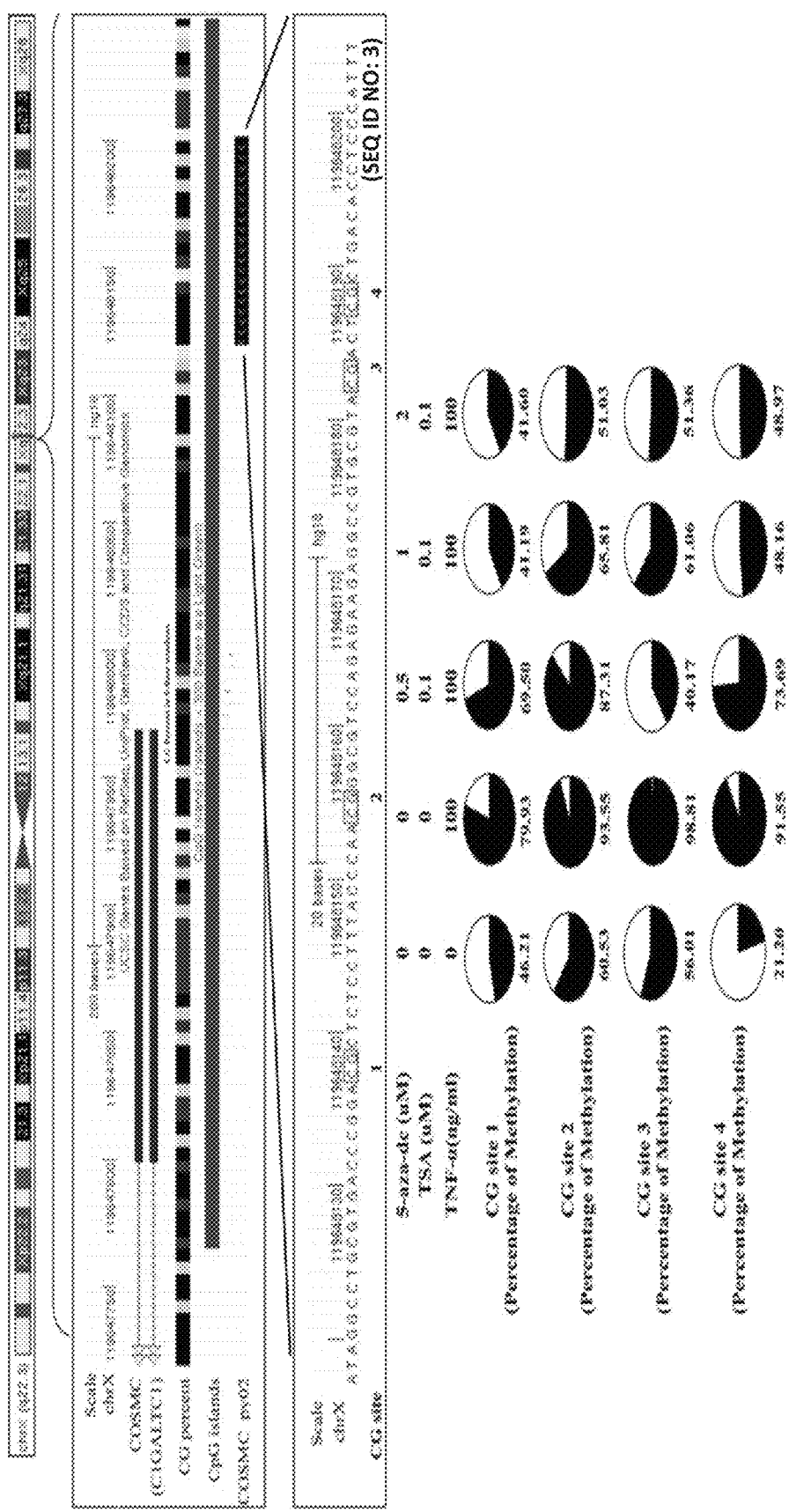
FIGS. 9A and B show that TNF-α-induced COSMC gene hypermethylation and Tn expression can be suppressed by demethylation agents (5-aza-dC).
Figure 9B:
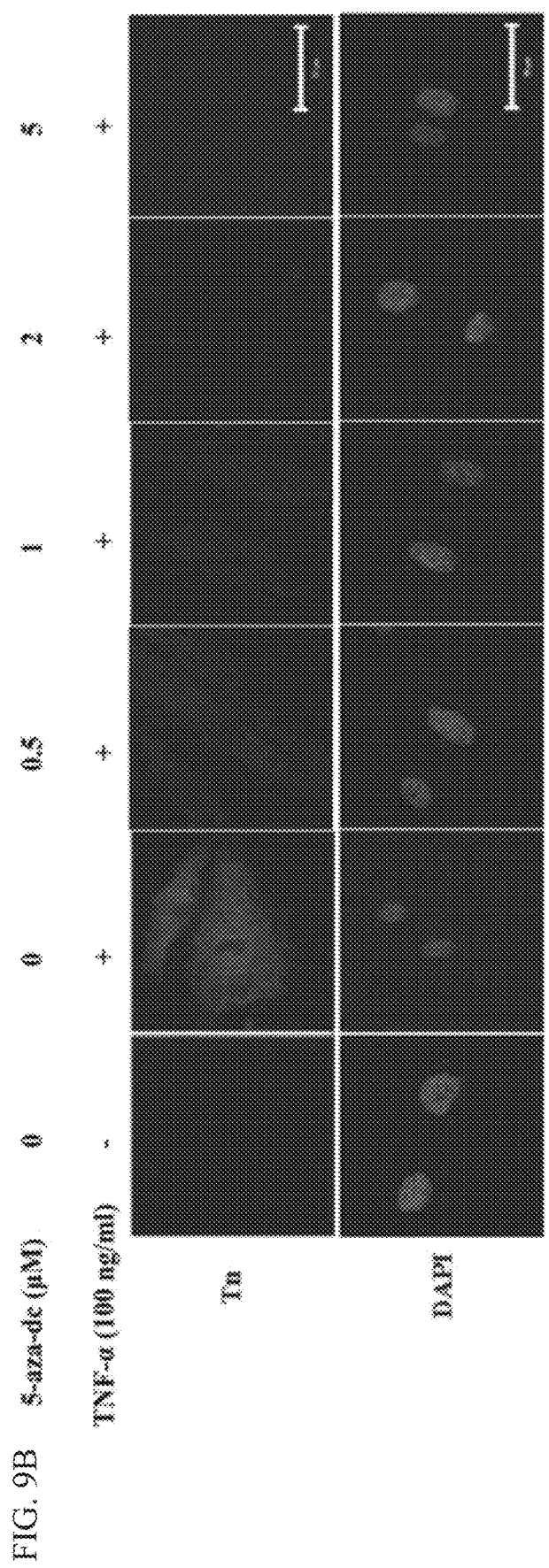
FIG. 9B. HGFs were co-treated with purified TNF-α and different concentrations of 5-aza-dC (0, 1, 2 and 5 μM) for 24 hours and then immunofluorescent stained with rabbit anti-Tn antibody (in red) and DAPI (in blue). Magnification 630×; Scale bar, 50 μm.

Example 9 TNF-α Up-Regulates Tn Expression Through Down-Regulation of the COSMC Gene To explore the possible molecular mechanism underlying cytokine-mediated up-regulation of Tn levels, the effect of TNF-α on the mRNA level of the COSMC gene was investigated. As shown in FIG. 8A, TNF-α (100 ng/ml, treatment for 24 hours) significantly down-regulated the COSMC mRNA in HGFs. By contrast, TNF-α did not significantly alter the T-synthase mRNA level. Similar results were observed for the protein levels of Cosmc and T-synthase in HGFs upon TNF-α treatment (FIGS. 8B, 8C and 8D). The effect of TNF-α on the down-regulation of the COSMC gene could possibly involve hypermethylation of the CpG islands in its promoter. Using bisulfite pyrosequencing to quantify the methylation change in the promoter of the COSMC gene, four CpG sites were significantly hypermethylated by TNF-α treatment (FIG. 9A). Pretreatment of HGFs with demethylating agents decreased the methylation of the four CpG sites in the COSMC promoter in a dose-dependent manner (FIG. 9A), and correspondingly, increased the expression of the COSMC mRNA and decreased the level of Tn (FIG. 9B). In the aggregate, our results suggest that cytokine-mediated up-regulation of Tn levels is due to down-regulation of COSMC, which involves hypermethylation of the COSMC gene promoter.

We claim:

1. A method of inducing an immune response in a subject to treat or prevent hyperoxia-induced lung injury, comprising administering to the subject a single dose of a vaccine,
    wherein the vaccine comprises about 0.1 mg to about 4 mg of a GalNAc-a-O-Ser/Thr (Tn) immunogen per dose and an adjuvant solution in a ratio of about 0.5 to about 2 (v/v),
    wherein the Tn immunogen is conjugated with a carrier polypeptide selected from: the amino acid sequence of Pro-Cys-Cys-Gly-Cys-Cys-Gly-Cys-Gly-Cys (SEQ ID NO:2), or Fc fragment-7 repeats of (SEQ ID NO:2)-N-maleimide or Fc fragment-7 repeats of (SEQ ID NO:2)-N-succinimidyl-6-maleimidocaproate.

2. The method of claim 1, wherein the about 0.1 mg to about 2 mg of a Tn immunogen per dose is administered four times at biweekly intervals.

3. The method of claim 2, wherein the method further comprises a step of having an additional immunization with about 0.1 mg to about 2 mg of the Tn immunogen one week after the fourth immunization.

4. The method of claim 1, wherein the administration of the single dose vaccine produces anti-Tn antibody with high serum titers than the titer of the control.

5. The method of claim 4, wherein the he serum titer of the produced anti-Tn antibody is at least 2 folds higher than the titer of the control.

6. The method of claim 1, wherein interleukine-6 (IL-6) and TNF-α levels or the activity of NF-κB in a subject is reduced after treatment with the vaccine.

7. The method of claim 1, wherein the subject has an elevated Tn expression.

8. The method of claim 7, wherein the Tn expression is upregulated by TNF-α and IL-6.

9. The method of claim 7, wherein the elevated Tn expression is commonly regulated by the cytokine-Cosmc signaling axis.

10. The method of claim 1, wherein the Tn immunogen and the carrier polypeptide are at a weight ratio of about 3 to about 8:about 1.

11. The method of claim 1, wherein the Tn immunogen has the following structure:

R is a carrier polypeptide

12. The method of claim 1, wherein the vaccine is-formulated as a single dose vaccine in a pharmaceutically acceptable formulation.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: artificial sequence
<220> FEATURE:
<223> OTHER INFORMATION: synthetic peptide

<400> SEQUENCE: 1

Cys Cys Cys Cys Cys Cys
1               5

<210> SEQ ID NO 2
<211> LENGTH: 10
<212> TYPE: PRT
<213> ORGANISM: artificial sequence
<220> FEATURE:
<223> OTHER INFORMATION: synthetic peptide

<400> SEQUENCE: 2

Pro Cys Cys Gly Cys Cys Gly Cys Gly Cys
1               5                   10

<210> SEQ ID NO 3
<211> LENGTH: 88
<212> TYPE: DNA
<213> ORGANISM: human

<400> SEQUENCE: 3
ataggcctgc gtgacccgga cgctctcctt tacccaacgg gcgtccagag aagaggccgt      60
gcgtacgact cgctgacacc tcccattt                                         88
```